(12) United States Patent
De La Cruz et al.

(10) Patent No.: US 6,546,782 B1
(45) Date of Patent: Apr. 15, 2003

(54) HIGH TEMPERATURE PRESSURIZED HIGH FREQUENCY TESTING RIG AND TEST METHOD

(75) Inventors: Jose De La Cruz, San Antonio, TX (US); Paul Lacey, The Woodlands, TX (US)

(73) Assignee: Southwest Research Institute, San Antonio, TX (US)

(*) Notice: Subject to any disclaimer, the term of this patent is extended or adjusted under 35 U.S.C. 154(b) by 0 days.

(21) Appl. No.: 09/669,270

(22) Filed: Sep. 25, 2000

(51) Int. Cl.$^7$ ................................................ G01N 3/56
(52) U.S. Cl. ................................................ 73/7; 73/10
(58) Field of Search .................................... 73/7, 10

(56) References Cited

U.S. PATENT DOCUMENTS

| | | | |
|---|---|---|---|
| 3,166,927 A | | 1/1965 | Sountag et al. ............... 73/10 |
| 3,302,447 A | | 2/1967 | Mertwoy et al. .............. 73/10 |
| 3,785,196 A | * | 1/1974 | Smith .......................... 73/64 |
| 3,913,337 A | | 10/1975 | Lindeman .................... 73/10 |
| 4,009,606 A | * | 3/1977 | Clebant et al. ............... 73/91 |
| 4,228,674 A | * | 10/1980 | Mertwoy ..................... 73/10 |
| 4,253,326 A | | 3/1981 | Muennich |
| 4,311,036 A | | 1/1982 | Kajdas et al. ................. 73/10 |
| 4,491,373 A | * | 1/1985 | Sugi et al. ................. 308/5 R |
| 4,939,922 A | | 7/1990 | Smalley et al. ............... 73/10 |
| 5,022,229 A | * | 6/1991 | Vitale ............................. 62/6 |
| 5,281,535 A | | 1/1994 | Wei et al. .................... 436/73 |
| 5,515,712 A | | 5/1996 | Yunick ............................ 73/9 |
| 5,865,070 A | * | 2/1999 | Bornhorst et al. ............ 74/603 |
| 6,070,456 A | * | 6/2000 | Cameron et al. ........... 73/53.05 |
| 6,109,617 A | * | 8/2000 | Laney ......................... 277/369 |

* cited by examiner

Primary Examiner—Daniel S. Larkin
Assistant Examiner—C D Garber
(74) Attorney, Agent, or Firm—Paula D. Morris & Associates, P.C.

(57) ABSTRACT

An apparatus is described which permits the lubricity of fuel compositions at or near temperatures and pressures experienced by compression ignition fuel injector components during operation in a running engine. The apparatus consists of means to apply a measured force between two surfaces and oscillate them at high frequency while wetted with a sample of the fuel composition heated to an operator selected temperature. Provision is made to permit operation at or near the flash point of the fuel compositions. Additionally a method of using the subject apparatus to simulate ASTM Testing Method D6079 is disclosed, said method involving using the disclosed apparatus to contact the faces of prepared workpieces under a measured load, sealing the workface contact point into the disclosed apparatus while immersing said contact point between said workfaces in a lubricating media to be tested, pressurizing and heating the chamber and thereby the fluid and workfaces therewithin, using the disclosed apparatus to impart a differential linear motion between the workpieces at their contact point until a measurable scar is imparted to at least one workpiece workface, and then evaluating the workface scar.

60 Claims, 13 Drawing Sheets

HIGH TEMPERATURE PRESSURIZED HIGH FREQUENCY TESTING RIG AND TEST METHOD

STATEMENT REGARDING FEDERALLY SPONSORED RESEARCH

The United States Government has a paid-up license in this invention and the right in limited circumstances to require the patent owner to license others on reasonable terms as provided for by the terms of Contract No. YXE-8-18033-01 awarded by the National Renewable Energy Laboratory.

FIELD OF THE INVENTION

This invention relates to an apparatus and method for testing lubricating properties of fluids and wear resistance of materials

BACKGROUND OF THE INVENTION

Fuel system components employed in some modern ground and aviation equipment rely on the fuel passing through them for lubrication of sliding contacts. Some of these components experience extreme temperature and pressure conditions in operating engines. One such component is the fuel injector used in diesel engines.

One way to examine the efficacy of fuel compositions as lubricants and the resistance of materials to the wear mechanisms experienced in fuel injectors would be to construct full scale working units and run them in test engines, examining them afterwards for wear. This approach is both costly and time consuming. It is of great utility in the transportation industry to predict the efficacy of fuel compositions in providing lubrication and the wear resistance of various materials of construction without having to construct and operate full scale equipment under conditions duplicating the operating conditions to which the equipment would be subject when in use.

To reduce time and cost, the properties of lubricating compositions are often tested using a testing jig. Typical equipment used for this purpose uses a mechanism to impart motion between two samples of material with the lubricant of interest interposed between the samples. The lubricating ability of the lubricant under study is determined either by studying the rate of wear of standard sample materials with different lubricants under the same conditions of load and motion, or to measure the amount of torque transmitted between a driving mechanism holding one sample and a driven mechanism holding the other sample when a given lubricant is interposed between the driving and driven samples. Both schemes have been employed to model components in operating equipment. The scheme utilizing the study of wear rates in sample materials has the added benefit that along with studying the lubricating ability of different lubricant compositions, the same equipment can be used to study the effect on wear of different combinations of materials or different surface finishes when they are examined with standard lubricating compositions.

Both schemes have been employed in bench top scale equipment and attempts have been made to correlate the results thus obtained with the results obtained from employing full scale equipment in an operating engine.

The wear rate in a component subjected to sliding contact is dependant upon many factors. Some of these factors are: materials of construction; surface finish; contact load; the relative rate of motion of the surfaces; and the nature of the lubricant and its film thickness. The environment in which a component is employed can also contribute to performance of a lubricant. Factors such as temperature and fluids present in addition to the lubricating composition employed must also be considered when constructing equipment that approximates conditions in operating engines. Numerous schemes for attempting to accomplish this end have appeared in the prior art.

U.S. Pat. No. 3,166,927 to Sonntag et. al. discloses an apparatus for measuring resistance to relative motion of two annular test surfaces having angular movement relative to one another. The apparatus disclosed is capable of imparting either rotary motion between two surfaces or oscillating motion (via an arm and eccentric) between the test surfaces. One of the two rods is a driving rod. One end of the driving rod is fastened to a motor, the other end is fitted with a mechanism for holding a test sample and a mechanism for contacting one surface of that test sample under controlled load against one surface of a second test sample. The end of the driving rod bearing the sample holder, the sample holder itself, and any sample contained in the sample holder resides in a lubricant sample well capable of containing a quantity of the lubricant composition under test.

The other rod of the pair is a driven rod. One end of the driven rod also resides in the sample well with the driving rod. The end of the driven rod within the lubricant sample well is also fitted with a mechanism by which a sample can be mounted on the end of the driven rod. The driven rod is supported so that when the driving rod sample is contacted against the sample fastened to the driven rod it is not displaced by the force of the contacting load. The end of the driven rod that is not within the sample well is fastened to a dynamometer and torque tube arrangement for measuring torque transmitted from the driving sample to the driven sample.

A scheme is disclosed wherein the sample lubricant and the testing surfaces are contained in a controlled temperature and atmosphere chamber for varying the testing conditions with respect to temperature and pressure. This arrangement is believed by the inventors to counteract the inaccuracies inherent in friction testing machines due to test sample axis misalignment and non-uniform wear of test sample surfaces during a testing procedure.

U.S. Pat. Nos. 3,302,447 and 4,228,674 to Mertwoy discloses an apparatus directed solely at testing the lubrication properties of hydraulic fluids under the conditions of temperature and pressure such fluids typically encounter in use U.S. Pat. No. 3,302,447 discloses the basic device, a set of chucks holding balls made of suitable material in rotatable contact, with provision for heating the hydraulic fluid under test, and applying pressure to the working faces of the balls used in the tests, subjecting the hydraulic fluid to loading conditions. U.S. Pat. No. 4,228,674 improves upon the former design, inverting the testing jig to counteract buoyancy of the testing samples in the hydraulic fluid under test, and providing for the ability to employ a fluid in the chuck driving mechanism having a different viscosity than the fluid under test, eliminating testing inaccuracies arising from fluids of different viscosity effecting the ability of the drive mechanism to rotate the chuck containing the test balls. A further improvement disclosed in the '674 patent is the use of a spring and tensioning mechanism to preload the test balls, substituting for lead weights employed for this purpose in the device disclosed in the '447 patent.

U.S. Pat. No. 3,913,337 to Lindeman discloses an apparatus for testing the lubricating properties of various fluids and the wear properties of various materials. In the disclosed apparatus, one of two motors, chosen for high speed operation or low speed operation, rotate a disk of test material between two stationary samples of test material. The stationary samples are in the form of a rod or block. One face of each stationary sample is held in contact with the faces of the disk by a caliper mechanism. Said caliper mechanism permits operator adjustment of the force applied to the faces of the disk of test material by the stationary samples. The test disk is arranged so that while rotating it passes through a bath containing the lubricating fluid under test. The entire mechanism except for the motors is contained in a sealed box, and provisions are made for heating and pressurizing the fluid under test. The disk is analyzed for wear at the end of an operator selected period during which the disk is rotated at an operator selected rotational rate while the stationary calipers impinge the stationary samples against the disk under an operator selected load. The apparatus provides for transducers which can measure the drag exerted against the rotational effort of the motor whereby the lubricating properties of the test fluid can be evaluated.

U.S. Pat. No. 4,253,326 to Munnich, et. al discloses an apparatus which may be employed to measure film thickness and moment of friction simultaneously. Additionally, it may be used to evaluate the wear properties of materials. The apparatus consists of two sample holders, the driving sample holder is mounted on a rotating shaft, the driven sample holder is mounted on a hydraulic device capable of linear motion along the axis of rotation of the rotating shaft. The sample holders are adapted to support samples of materials having test faces with said test faces in contact. The material employed in the test faces is employed either to test the properties of a lubricant or to test the wear properties of the materials which form the test faces. The apparatus utilizes strain gages to measure the torque imparted to the driven sample holder, and thus provides a method of calculating the frictional forces imparted between the driving and driven sample. A capacitance device is also provided to dynamically measure the thickness of the lubricant film residing between the two sample faces during the testing procedure. Lubricating properties can be calculated dynamically as a function of load, sample rotational rate, and film thickness. The test samples and sample holders are mounted in a sealed chamber permitting variation of lubricant temperature and pressure, and a design is disclosed wherein the loading force between the two sample faces may be varied as a function of time by oscillating the pressure of the hydraulic system that applies a loading force to the contacted samples.

U.S. Pat. No. 4,311,036 discloses an apparatus for testing the lubricating properties of liquids over a range of pressures and rubbing speeds which are varied between a test surface fully wetted in the test lubricant and a condition of dry friction between the test surfaces. The disclosed apparatus consists of a rotating cylinder of test material immersed in a sample of the lubricant under test. Two fixed specimens contact the surface of the test material cylinder normal to the cylinder axis of rotation. A load is placed on the fixed specimens. The disclosed apparatus incorporates strain gages to measure the resistance of the cylinder to rotation when loaded by the fixed specimens. The temperature of the test lubricant is measured and controlled, and in addition the lubricant film thickness is measured. Measurement of lubricant film thickness is achieved by measuring the electrical resistance between the counter specimens contacting the cylinder and the test material cylinder. Further features of the subject apparatus are screw adjusters interconnected by a flexible worm drive to permit both manual and electric motor adjustment of the force with which the counter specimens are impinged on the test material cylinder face.

U.S. Pat. No. 4,939,922 to Smalley et.al. discloses an apparatus for evaluating sliding friction between materials and the wear rate of materials such as those used in conventional 4 cycle internal combustion engine valve trains. The disclosed apparatus consists of a test jig that supports separate devices for applying and measuring the forces generated between machine elements when a reciprocating member runs in contact a rotating eccentric member. The face of the reciprocating member in contact with the eccentric and the eccentric itself are made of a material whose wear or friction properties are to be tested. The eccentric is rotated by a motor connected to the shaft upon which it is mounted. The shaft is equipped with a torque measuring and recording device as well as a vibration damping device. The reciprocating and eccentric test materials are contained within a sealed chamber. In use the sealed chamber is filled with the lubricant whose lubricating properties are under test. The chamber is equipped with a thermostat and a heating loop that passes the test lubricant through a heating device to maintain or raise the temperature of the lubricant under test in a preset fashion. Lubricating properties are determined by plotting energy consumed in rotating the test specimen as a function of lubricant temperature for a given load between the faces of the materials under test.

U.S. Pat. No. 5,281,535 to Wei, et.al. discloses an apparatus and method for examining the friction between two test surfaces exposed to a variety of gaseous and liquid fluids. The test surfaces of the disclosed apparatus are contained in a sealed chamber capable of supporting a partial vacuum and equipped with facilities to generate plasma when the test fluid is a gas (e.g. atomic oxygen plasma generated in an oxygen atmosphere). The testing apparatus disclosed comprises a horizontally oriented disk of test material affixed to a shaft passing through the bottom of the test chamber. The shaft is rotated by an electric motor. A second test surface (a "contacting pin") is supported on an arm above the rotating test surface. The "contacting pin" has the form of a rod with a rounded end, said rounded end contacting the rotating test surface. The supporting arm of the second testing surface contains a screw device for varying the pressure of the contact between testing surfaces. The arm itself is affixed to a jig that is adapted to a path of reciprocating motion normal to the axis of rotation of the rotating testing surface. The reciprocating device is actuated by an electric motor, the shaft of which is passed through a seal in the side of the testing chamber. The frictional forces between the contacting pin and the disk of test material are measured by a strain gauge interposed in the mount supporting the "contacting pin". Additionally, the rotating sample may be examined at the termination of the test for wear patterns and degree of material worn away during the test. Additionally disclosed is a scheme for introducing more than one fluid into the chamber during a testing cycle.

U.S. Pat. No. 5,515,712 to Yunick discloses an apparatus and method for determining the power consumed by an internal combustion engine when it is rotated. The apparatus consists of an electric motor capable of rotating a gasoline engine at operating speeds, a torque meter affixed to the gasoline engine output shaft, and various devices affixed to the fluid pathways within the gasoline engine for measuring component displacement, rotational speed, air flow, and gas entrained in the lubricating fluid of the gasoline engine. The testing method disclosed consists of driving the engine with one set of components and lubricant installed, then changing out components or lubricant and rerunning the test, comparing the energy consumption required for the two configurations.

Some of the testing schemes disclosed in the prior art are adequate to test the relative properties of fluids intended primarily to provide lubrication to machine parts in sliding contact. Other apparatus and testing methods disclosed in the prior art are good at predicting the intrinsic wear properties sliding contact between two materials in unusual environments such as space. These prior art schemes are not adequate to accurately test the lubricating properties of fuel compositions or the antiwear properties of materials such as is required when performing lubricity or wear determination for materials and lubricants employed in fuel injection equipment. ASTM testing standard D6079 has been shown to correlate well the wear mechanisms which the sliding components in full scale fuel injectors experience during operation, and is incorporated by reference here within. ASTM testing standard D6079 specifies a high frequency reciprocating contact is required to simulate the wear mechanisms present in fuel injection equipment. ASTM testing standard D6079 further specifies that test specimens used in testing the lubricity of diesel fuel compositions be a 6.00 millimeter ball contacting a 10 millimeter diameter disk, with the area of contact under a load of 200 grams. The standard additionally requires that the test samples be moved relative to one another through a linear reciprocating stroke of one millimeter at a rate of 50 stroke cycles per second. The standard also requires that the point of contact between samples be completely immersed in the fluid the lubricating properties of which are being tested. It is known in the prior art that submerging test samples in the fluid under test entails additional problems which cause the test to deviate from correlating well with the wear experienced by full scale equipment under operating conditions. A practical testing jig must therefore address the problem of maintaining the point of contact under a covering of the lubricating fluid under test, without having it submerged in a bath so deep that viscosity and buoyancy effect the accuracy of the test. This problem is addressed in the ASTM testing standard D6079 by regulating the sample size placed in the apparatus and avoiding excessive heating of the sample. Other requirements of the standard are designed to eliminate sources of error in correlating the wear pattern generated on the test materials with wear experienced in full scale equipment under operating conditions.

Conventionally, testing of lubricity in sliding contact is accomplished by interspersing a lubricating fluid between a mobile and stationary work face and measuring the relative ability of various lubricating fluids to reduce the drag imparted to the mobile work face by the stationary work face in contact with it. Alternatively, a testing apparatus may utilize a driving and driven work face, and the effort required to resist motion in the driven work face is measured. In addition to measuring the amount of toque transmitted through a lubricant film, the type and amount of wear (generally measured as loss of material in one or both work faces) is observed on the workpieces after a period of sliding contact has been maintained between two work faces with the lubricant interposed between the work faces. The amount of material loss undergone by the samples with a standard lubricant interposed between sample faces will yields a method of evaluating the antiwear properties of the materials of construction employed in the test pieces. Standard materials and surface finishes can give a relative understanding of the lubricating properties of different lubricant compositions.

The above cited prior art apparatus may be divided into two broad categories: open chamber and sealed chamber equipment. The open chamber equipment is unsuitable for testing fuel compositions at the temperatures typically experienced by a fuel injector in an operating engine. Even if it were possible to keep the volatile fuel composition proximate to the friction surfaces of the test apparatus, the explosion hazard represented by open air testing of fuel compositions at or near their flash point would be unacceptable from a safety standpoint. Therefore, all apparatus which do not provide for closed chamber containment of the fluid undergoing lubricity testing represent a hazard when used to test diesel fuel compositions for lubricity at temperatures similar to those experienced in a fuel injector environment.

Closed chamber equipment described in the prior art may be divided into two broad categories, that which affords reciprocating contact between test surfaces and that which employs some other form of rubbing interaction between the surfaces. Since a reciprocating interaction is required to simulate wear conditions existing in a fuel injector, only a testing apparatus that provides for reciprocating contact would be adaptable to testing the wear resistance of materials and the lubricity of diesel fuel compositions in an apparatus which simulates the conditions experienced within a fuel injector apparatus installed in an operating engine. On this basis, only U.S. Pat. Nos. 3,166,927, and 5,281,535 relate equipment that provides for both reciprocating contact between test specimen surfaces and a construction incorporating a sealed chamber. All of the other prior art examples can not a priori meet the requirements for carrying out testing in accordance with ASTM standard D6079.

The apparatus disclosed in the '927 patent provides for contact between planer specimens, precluding meeting the ASTM D6079 requirement to simulate fretting type wear by utilizing contact between a flat specimen surface and a spherical surface. Further, the design of the apparatus is such that there must be evenly distributed contact about the radius of the contacting surfaces, precluding introduction of a specimen containing a single off-axis spherical feature. Spherical contact could be achieved in the apparatus disclosed in the '927 patent by machining spherical features evenly distributed about the radius of the one test surface. Using such a scheme however would require very precise machining of the specimen to insure that the spherical surfaces distributed about the radius were in precisely the same plane. This would be required because the design of the disclosed apparatus applies contacting pressure distributed evenly about the specimen's radius. Any contacting surface protruding beyond the others would prevent the others from contacting the flat specimen until it had worn away an appropriate amount.

Secondly, the apparatus disclosed in the '927 patent is directed at measuring lubrication properties by measuring the torque transmitted from a driving sample to a driven sample. ASTM standard D 6079 calls for a mobile sample surface to be displaced across a fixed sample surface. Since the moving sample surface disclosed in the '927 patent (driving sample surface) is capable of displacing the stationary sample surface (driven sample surface), the disclosed apparatus is not capable of measuring wear properties in the manner specified by ASTM D 6079.

U.S. Pat. No. 5,281,535 discloses an apparatus which employs a worm drive carriage to impart reciprocal motion to a first sample surface relative to a second sample surface. The second sample surface is mounted on a spindle which can be rotated such that the reciprocal motion is perpendicular to the axis of rotation. The spindle and worm drive carriage are enclosed within a sealed chamber and drive by motors mounted externally and coupled with magnetic coupling devices. The arrangement permits reciprocal motion of one test surface against a second stationary test surface. The disclosed apparatus uses a magnetic coupling device to drive the worm gear assembly contained within the chamber. The reciprocal movement of the worm driven carriage is accomplished by reversing the driving motor. The apparatus disclosed in the '535 patent is not capable of precise stroke control at the frequency required by ASTM standard D6079, and therefore is not suitable to carry out the test protocol specified by that standard.

SUMMARY OF THE INVENTION

One aspect of the present invention is that it affords making measurements of the lubricating properties of fuel compositions in keeping with ASTM standard D 6079. Another aspect of the present invention is that it affords lubricity property testing under the extremes of temperature and pressure to which machine elements are typically exposed when located in a combustion chamber environment, such as is the case for diesel engine fuel injectors.

Another aspect of the present invention is that the apparatus affords a method of testing the lubricating properties of fuel compositions near their flash point without danger of fire or explosion.

Another aspect of the present invention is to provide a method testing the wear properties of different materials and combinations of materials in reciprocating wear contact in the presence of fuel compositions under conditions of high temperature and high pressure. Another aspect of the present invention is to provide an apparatus which contains such safety features that the danger of fire and explosion inherent in testing fuel compositions at or near their flash point is minimized in the event of an accidental detonation or combustion of such a sample. Yet another aspect of the present invention is to provide an apparatus that minimizes the maintenance and impact of mechanical seals by providing a testing chamber that is sealed with a compressed fluid that is constantly renewed.

Other aspects of this invention will appear from the following description and appended claims, reference being made to the accompanying drawings forming a part of this specification wherein like reference characters designate corresponding parts in the several views.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF DRAWINGS

Figure 1:
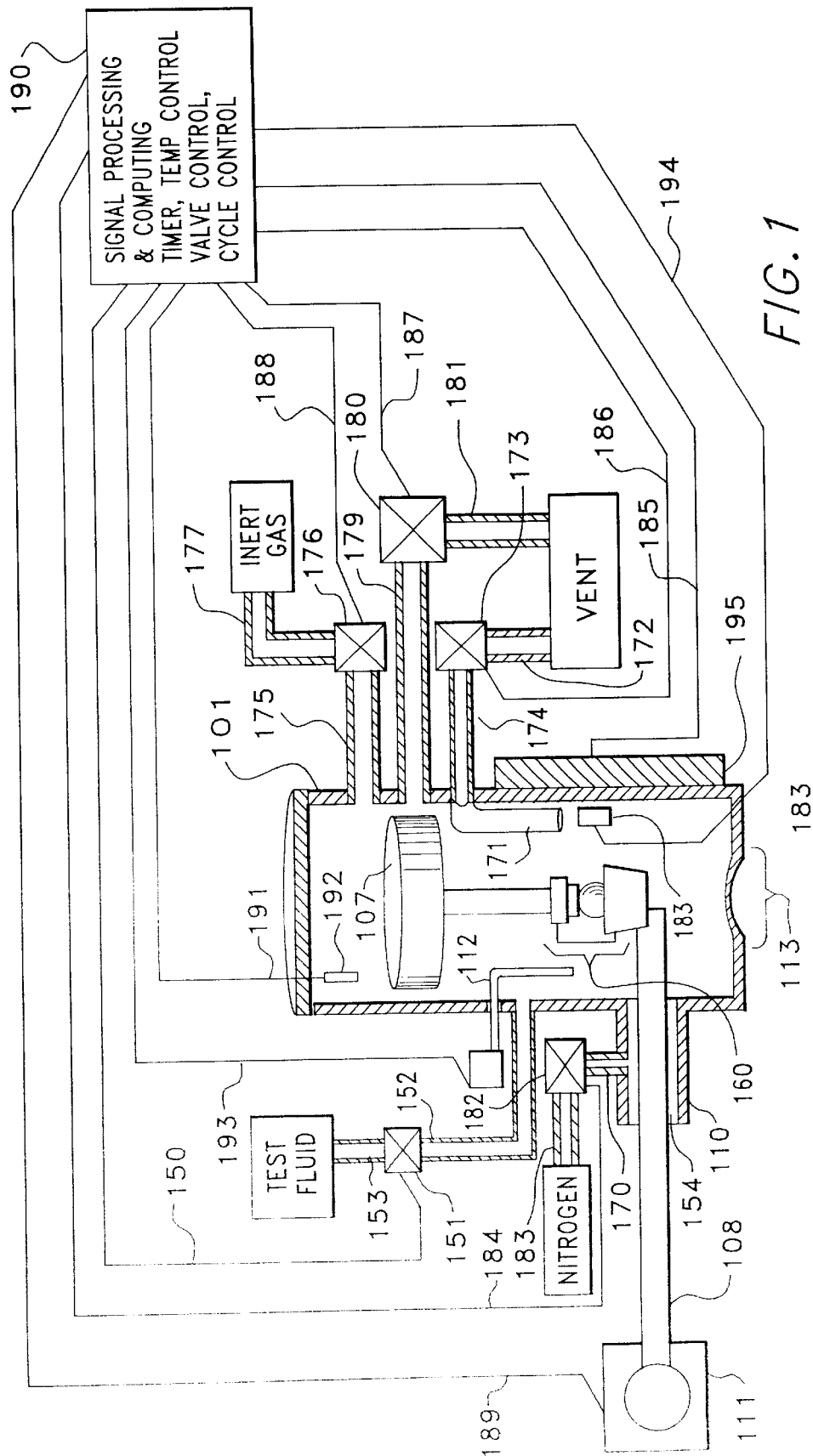
FIG. 1 is a schematic block diagram of the arrangement and connectivity of the elements of the testing apparatus and the control and sensor lines utilized by the automatic control device.

FIG. 1 is a schematic diagram of the subject testing apparatus, illustrating the mechanical features and the control elements embodied in the invention. With reference to FIG. 1, the apparatus consists of testing chamber 101, which contains workpiece holding and contacting assembly 160, workpiece loading device 107 and a variety of sensors disclosed below. Appended to testing chamber 101 is actuator rod support arm 110. Actuator rod support arm 110 is fitted with conduit 170, through which inert gas is passed into the bore through actuator rod support arm 110. Gas flow through conduit 170 is controlled by associated valve 182 and conduit 183. Valve 182, in embodiments having automatic valves, is actuated by control line 184, further details of these features are disclosed below.

With further reference to FIG. 1, actuator rod assembly 108, having a first and second end, passes through actuator rod support arm 110 and into testing chamber 101. The first end of actuator rod 108 resides inside of testing chamber 101, and interacts with the workpiece holding and contacting assembly 160 such that when actuator rod 108 is displaced, it imparts precise differential motion to workpieces held in contact by workpiece holding and contacting assembly 160. The force of contact between workpieces contained in workpiece holding and contacting assembly 160 is regulated by workpiece loading assembly 107. Details of workpiece holding and contacting assembly 160 are specified below, as are details of workpiece loading assembly 107.

With further reference to FIG. 1, the second end of actuator rod 108, which resides in the ambient environment outside of testing chamber 101, is attached to motion generator 111. The attachment between actuator rod 108 second end and motion generator 111 is such that actuator rod 108 transforms motion from motion generator 111 into precise linear motion which it imparts to at least one of the workpieces held in workpiece holding and contacting assembly 160.

With further reference to FIG. 1, inert gas is supplied to testing chamber 101 via conduit 175. Attached to conduit 175 is valve 176. In one embodiment of the present invention, valve 176 is an electrically or pneumatically actuated valve. In such an embodiment, an electronic control device actuates valve 176 in response to an electric signal passed to the electronic control device via control line 188 by supplying the electric or pneumatic power required to actuate valve 176. The electric signal required by the control device to actuate valve 176 is equally well supplied by a manual switch, a computer under operator control, or a computer running a program in response to a time or event sequence, or in response to a signal generated by pressure sensor 192 in response to pressure conditions within chamber 101. The signal generated by pressure sensor 192 is passed to said computer control 190 via sensor line 191. In other embodiments a mechanically actuated valve 176 may be equally well employed and control line 188 eliminated.

With further reference to FIG. 1, testing chamber 101 is vented via conduit 179. Fluid flow through conduit 179 is controlled by valve 180. Fluid vented through valve 180 is further conducted along attached conduit 181 to a suitably arranged venting system such as is familiar to one skilled in the art of handling flammable or toxic fluids. Valve 180 may be an electrically, pneumatically, or mechanically actuated valve. Actuation of valve 180 may be manual, or may arise from an electric signal passed to an electric control device via control line 187, said control device supplying the pressure or electricity necessary to actuate valve 180. If an electric signal is used to ultimately actuate valve 180, such a signal is equally well supplied by a manual switch, a computer under operator control, or a computer running a program. In an embodiment in which a computer program actuates valve 180, the signal can arise in response to an elapsed period of time or an event sequence, or in response to a signal arising from pressure sensor 192, said signal being transferred to computer 190 via sensor line 191 in response to a change in pressure within testing chamber 101.

With further reference to FIG. 1, testing chamber 101 contains condensed fluid during a test. The lubricant media may be any liquid, but for the present invention testing apparatus fuel compositions are preferred, and most preferred are fuels of the type used in or of potential utility in compression ignition and glow ignition diesel engines. The lubricant properties of the condensed fluid, hereinafter termed lubricant media, are being tested in the apparatus. The volume of lubricant media used in the testing chamber must be adjusted so that it does not introduce buoyancy effects into the test. The volume of lubricant media is adjusted using fluid eductor tube 171 which is joined to conduit 174. Conduit 174 is attached to valve 173, which controls the flow of fluid from testing chamber 101. When valve 173 is actuated open, so long as the testing chamber 101 contains pressure in excess of that of the ambient environment, fluid is passed up eductor tube 171, through conduit 174, and thence through valve 173. From valve 173, it is further conducted along conduit 172 and thence passed into a suitably arranged venting system such as is familiar to one skilled in the art of handling flammable or toxic fluids.

Condensed fluid residing in the bottom of testing chamber 101 will pass up the eductor tube until the level of the condensate falls below the opening of eductor tube 171. After that only vapor phase material will pass up the eductor tube 171. This principle may be used to adjust the level of condensate in testing chamber 101.

Valve 173 may be an electrically, pneumatically, or manually actuated valve. Actuation of valve 173 may be accomplished by passing an electric signal to an electric control device via control line 186, said control device in turn supplying the pressure or electricity necessary to actuate a pneumatic or electrically actuated valve 173 in response to such an electric signal. If an electric signal is used to ultimately actuate valve 173, in different embodiments of the present invention such a signal is supplied by a manual switch, a computer under operator control, or a computer running a program. A computer program could actuate valve 173 in response to a time or event sequence, or in response to a signal arising from level sensor 183 passed via sensor line 194 to computer controller 190 in response to a change in the level of lubricant within chamber 101.

With further reference to FIG. 1, in different embodiments of the present invention, motion generator 111 may be under operator control, the control of a computer under operator control, or control of a computer running a program. In one embodiment of the present invention, motion from the motion generator 111 is transferred to actuator rod 108 through an electrically actuated coupling. Operation of the coupling is controlled by an electric signal sent through control line 189.

With further reference to FIG. 1, testing chamber 101 is also fitted with heater 195. Heater 195 may be under operator control, the control of a computer under operator control, or control of a computer running a program. Control of heating the testing chamber with heater 195 may be accomplished by using an electric signal passed to an electric control device via control line 185, said control device supplying the hot fluid or electricity necessary to effect heating in response to such an electric signal. In one embodiment of the present invention, heater 195 is an electric resistance heating device, and the control device supplies electric power in response to a signal applied to control line 185. In other embodiments, heating device 195 is a fluid heat exchanger, and control line 185 controls the flow, the temperature, or both the temperature and the flow of the fluid passing through said fluid heat exchanger. Other methods of controlling the temperature in testing chamber 101, such as are well known to one skilled in the art, may also be employed with equivalent results.

The signal applied to control line 185, which controls the operation of heating device 195, may be supplied manually, by a computer under operator control, or by a computer running a program that supplies control signals in response to an event sequence, an elapsed time, or in response to a signal from temperature sensor 112. Utilizing signals from temperature sensor 112 enables dynamic control of the temperature with testing chamber 101. Temperature sensor 112 may be an electrical resistance device, a pneumatic switch type of device, a thermocouple device, or any other device generating a signal in response to a change in temperature such as is well know to one skilled in the art. In the preferred embodiment, temperature sensor 112 is a thermocouple connected to a computer via appropriate signal conditioning hardware such as a Watlow 96 Process Temperature Controller™ #96A1-CAAV-00RG or a Powers 535 Process Temperature Controller #935-200000B0000™. In this manner, the system can be operated as a closed loop temperature control system.

In one embodiment of the present invention, computer 190 is loaded with software and hardware suitable for controlling the temperature of the interior of test chamber 101 by means of temperature sensor 112 and heater 195. In addition, the level of the test fluid in test chamber 101 is automatically controlled using sensor 183 and valve 173 and its related conduits. The actuation of inert gas valves 173, 176, 180 and 182, and the coupling and decoupling of motion generator 111 and actuator rod 108 is also under computer control, effectively controlling the differential motion between workpieces held in workpiece holding and contacting assembly 160. Examples of such hardware and software combinations include a PC type computer interfaced to an IDM Power-Master™ speed controller and IDM Power-Master™ signal conditioner.

With further reference to FIG. 1, the operation of the testing apparatus will be described. The method of using the apparatus is described using ASTM testing standard D6079 as an example, and though the present invention apparatus is well suited to carry out the essential features of this testing standard, other testing protocols are equally well carried out using the same general equipment and procedures. The apparatus is disassembled and cleaned according to ASTM specifications imparted in ASTM testing standard D 6079. Workpieces conforming to testing standard D 6079 are inserted into the workpiece holding and contacting assembly 160 and placed under load by workpiece loading device 107 to a value in accordance to the ASTM testing standard D 6079.

If the lubricant media to be tested for its lubricating properties is liquid under ambient conditions, a quantity of the fluid under test is charged into testing chamber 101, and the testing chamber is sealed. If it is not a liquid under ambient conditions, the lubricant media is introduced after testing chamber 101 has been sealed and purged.

When assembled, testing chamber 101 is purged with inert gas by repeatedly pressurizing testing chamber 101 to a predetermined pressure and venting the inert gas from testing chamber 101 via valve 180 and conduits 179 and 181. In preparation for a test, testing chamber 101 is pressurized via valve 176 one final time to a predetermined value. Simultaneously, high pressure gas flow is applied to support arm 110 via valve 182 and conduit 170. When actuator rod 108 is within the bore of actuator rod support arm 110, the gas builds up pressure in the annular space 154 between the two. In the best mode of practicing the subject invention, the gas pressure supplied by valve 182 to the annular space 154, acts to seal testing chamber 101 from the ambient environment. Additional features of this seal will be further disclosed below.

If lubricant media is a gas under ambient conditions, one such example being dimethyl ether, testing chamber is purged with inert gas as detailed above using repeated pressure/vent cycles, then vented to near ambient pressure. A quantity of the gaseous fluid to be tested is then charged into testing chamber 101 via conduit 152. Flow through conduit 152 is controlled by valve 151. A source of the gaseous lubricant media is connected to the inlet side of valve 151 via conduit 153. Additional sources of gaseous reagents as well as inert gas for purging the apparatus may be connected to conduit 153 through tee and valve arrangements such as are well known to one practiced in the art. Alternative embodiments of the subject invention may also include a separate valve and conduit affixed directly to testing chamber 101 for each gas contemplated to be introduced to testing chamber 101. Once a sufficient quantity of the gaseous lubricant media has been condensed into testing chamber 101, the testing chamber is pressurized with inert gas to a predetermined pressure. The pressure is determined by the environmental conditions that will be simulated during the test. In embodiments wherein the lubricant media is not inflammable when heated, purging the apparatus with inert gas prior to charging it with lubricant media is not required. In such testing conditions, conduits 175 and 177 and valve 176 may be eliminated from the testing apparatus.

In cases wherein the lubricant media has a high vapor pressure, the apparatus is charged with an amount of lubricant media condensate that considerably submerges the contact point of the workpieces in the sealed chamber. This is done to insure that the contact point will still be submerged after the testing chamber is heated to the test temperature. When the condensed lubricant media is heated, a portion of the condensate will vaporize until enough of the lubricant media has vaporized that the vapor phase material is in equilibrium with the condensate. Submerging the contact point prior to heating insures that it will still be immersed when enough of the lubricant media condensate has vaporized to establish an equilibrium vapor pressure within the testing chamber. This is to say that during heating, the pool of condensate will not have vaporized to a point that leaves the contact point between workpieces in the vapor, rather than in the condensate, following heating of the testing apparatus and condensate sample.

Once the testing chamber has been charged with testing materials, the chamber is heated to a predetermined value using heater 195 and feed the feedback loop comprising sensor 112 and sensor line 193 if the apparatus is so equipped. In one embodiment of the present invention employing computer control of the equipment, during heating and the conduct of the experiment, the gas pressure within testing chamber 101 is controlled by pressure sensor 192, control line 191, and vent valve 180 in a closed loop feed back arrangement. Fluid level covering the workpieces is also controlled by a feed back loop comprised of level sensor 183, sensor line 194, and fluid vent valve 173. If testing chamber 101 is not equipped the various sensors and control hardware and software described above, pressure and level are adjusted manually during the course of the experiment by the apparatus operator.

When the apparatus has been heated to a predetermined temperature and the pressure and level of testing fluid has been adjusted as required, differential motion between workpieces contained in the workpiece holding and contacting assembly 160 is imparted using motion generator 111. The present invention is suited to producing simulation of fretting wear of materials in accordance with ASTM testing standard D 6079 as well as being adaptable to carrying out lubricant tests in accordance with other testing protocol. ASTM testing standard D6079 specifies sliding a fixed spherical surface of specific curvature across a fixed plane surface, cyclically, along a linear 1 millimeter stroke path with a fixed load applied to the contact point of the two workpieces.

In one embodiment of the present invention, motion generator 111 is also capable of being adjusted for longer or shorter stroke paths, and for a higher or lower stroke frequency than the 50 cycles per second specified in ASTM standard D 6079. The parameters of stroke path and frequency are set by the operator prior to assembling the testing apparatus, with starting and stopping of the differential motion imparted by motion generator 111 being under computer or operator control during the test.

Materials and methods of construction are chosen for actuator rod 108, workpiece holding and contacting assembly 160, and motion generator 111 such that they are sufficiently robust that the linear differential motion imparted by motion generator 111 is translated to the workpiece contact point within workpiece holding and contacting assembly 160 without undue flexing of the assemblies, which would result in shortening the stroke length or departing the stroke trajectory from linear under the conditions of load maintained during a test.

With further reference to FIG. 1, Actuator rod 108 is supported by actuator rod support arm 110 which is rigidly fixed to testing chamber 101. Actuator rod support arm 110 provides a means of containing gas within chamber 101 to pressures exceeding 200 psig, while providing a means of constraining actuator rod 108 to movement normal to the major axis of chamber 101 when it is actuated.

With further reference to FIG. 1, in embodiments of the present invention employing computer control 190, the duration of the test is controlled by the computer. Differential motion between workpieces contained with workpiece holding and contacting assembly is commenced and ceased according to a preset interval supplied to the control program by the operator. Motion generator 111 is coupled to or decoupled from actuator rod 108 in response to a control signal supplied to control line 189.

In one embodiment, motion generator comprises an eccentric assembly mounted on a shaft. The shaft is connected to a source of rotational power by an electrically actuated clutch device which couples or decouples the eccentric to the rotational power in response to a signal appearing on control line 189. Further details of motion generator 111 are detailed below.

With further reference to FIG. 1, yet another feature incorporated into testing chamber 101 is blow-out panel 113. This section of chamber, the construction of which is detailed below, is designed to fail, relieving pressure in a controlled manner, in the event that a pressure excursion that could not be equalized by venting testing chamber 101 through valve 180 should occur within the testing chamber. An example of such an event would be the pressure wave associated with an explosion occurring in testing chamber 101 during a test.

Figure 2:
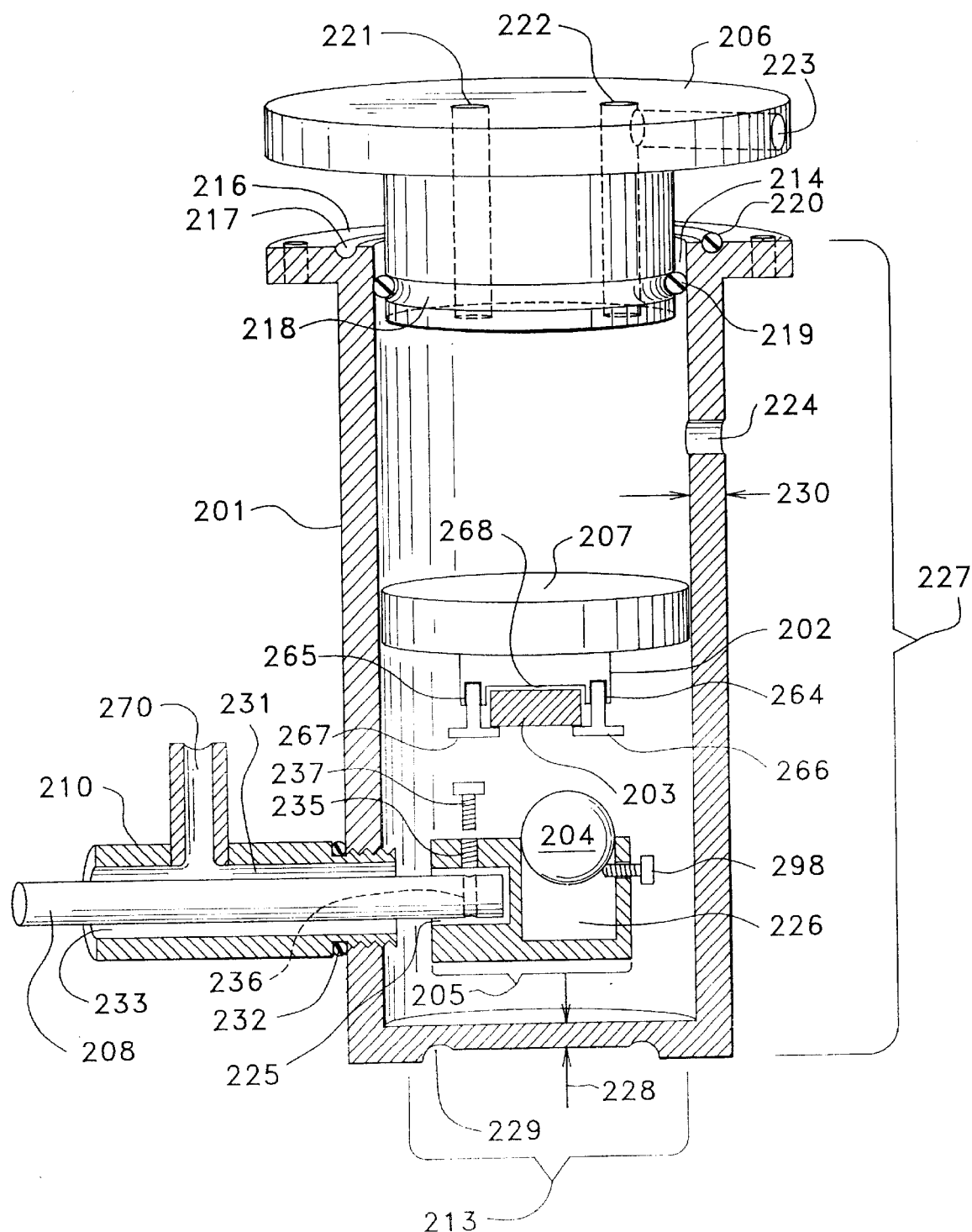
FIG. 2 is a cutaway elevation view of the testing chamber, cap, and actuator rod support arm with the actuator rod, workpiece loading device and workpiece chucks installed.

Further details of the mechanical features of testing chamber 101 are disclosed in FIG. 2. FIG. 2 is a cutaway elevation view of the testing chamber and the components it contains when assembled for a test. With reference to FIG. 2, testing chamber 201, which is equivalent to testing chamber 101 of FIG. 1 and it's equivalents disclosed below, is in the form of a hollow cylinder with one end closed by blow out panel 213 and the other end having opening 214. Blow out panel 213 is equivalent to blow out panel 113 of FIG. 1 and its equivalents disclosed below. In use, testing chamber 201 is oriented with the long axis of the cylinder approximately vertical, with blow out panel 213 facing down and testing chamber opening 214 facing up. In this orientation, actuator rod support arm 210, which is equivalent to actuator rod support arm 110 of FIG. 1 and its equivalents disclosed below, is oriented more or less horizontally.

With further reference to FIG. 2, when in use testing chamber 201 is sealed with cap 206 prior to running a test. Cap 206 may employ any form of seal which is sufficiently robust to withstand pressures in excess of 200 psi and chemical attack by the fluids employed in the test. Examples of such seals are well known to those practiced in the art and include flange and gasket seals, o-ring seals, knife edge and metal gasket, and threaded cap and receiver, either internally or externally threaded. When o-rings seals are employed to perfect a seal between testing chamber 201 and cap 206, and o-ring 220 may be placed in a groove such as groove 217 machined into flange face 216. With equal effect, an o-ring 219 may alternatively be placed in a groove such as 218 machined into cap 206 to effect a seal between cap 206 and the inside wall of testing chamber 201.

Figure 10A:
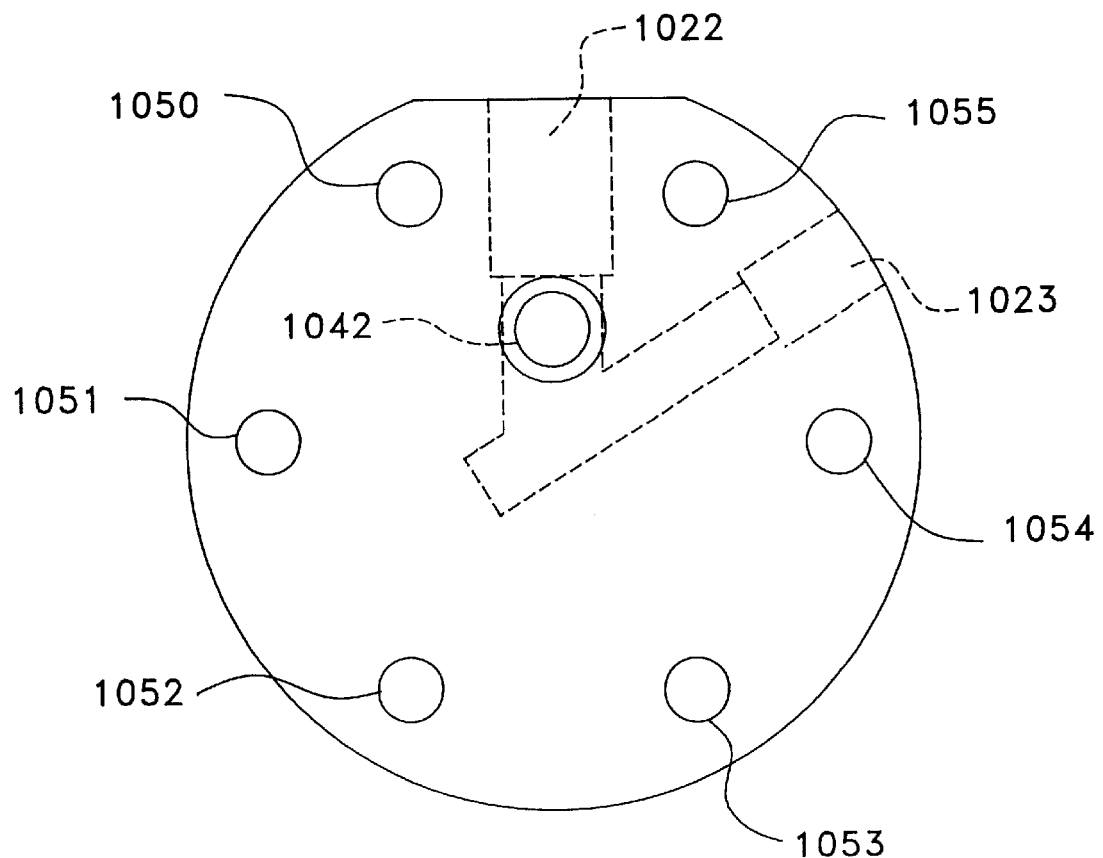
FIG. 10 is a plan view of an embodiment of the testing chamber cap.
Figure 10B:
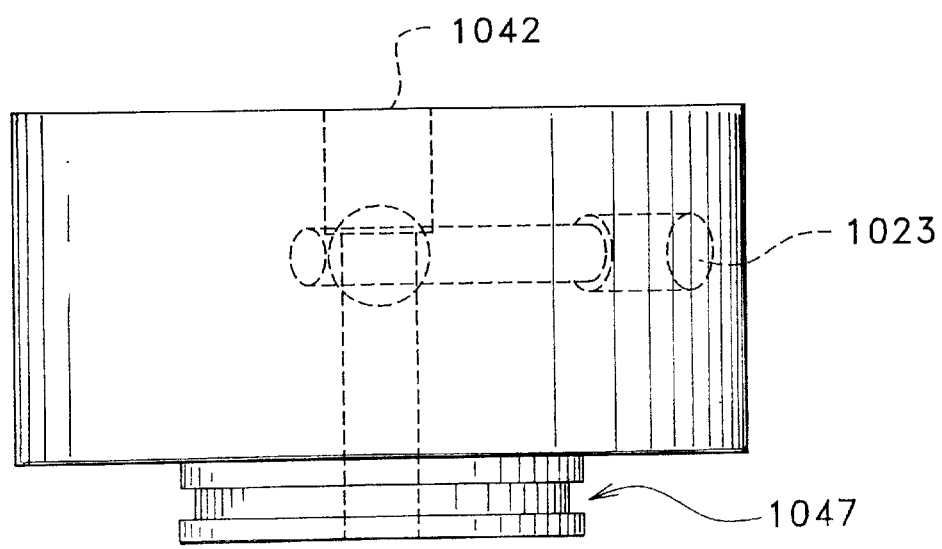

With further reference to FIG. 2, cap 206 also contains bored through conduits 221 and 222, and conduit 223 which is blind bored laterally into the side of cap 206 until it intersects conduit 222. These conduits serve to provide a method of passing fluids into and out of assembled testing chamber 201, and to pass conductors carrying signals from sensors such as thermocouples and level sensors located within testing chamber 201. In other embodiments the side walls of testing chamber 201 may contain conduits such as conduit 224 which can serve the same purpose as conduits 221, 222, and 223. FIG. 10 discloses an additional embodiment of cap 206.

With further reference to FIG. 2, testing chamber 201 contains flat workpiece chuck 202 and spherical workpiece chuck 205. Flat workpiece chuck 202 is adapted to hold flat workpiece 203. Flat workpiece chuck 202 is comprised of a shallow well 268 fashioned into a block of material fastened to workpiece loading device 207. Well 268 is given a depth less than the thickness of workpiece 202. Holes 264 and 265 are blind bored into the lip surrounding well 268 about 180 degrees apart. The holes are tapped to accommodate fasteners 267 and 266. Fasteners 267 and 266 have heads of sufficient diameter that they contact a workpiece 203 placed into well 268 when they are inserted into holes 264 and 265 and tightened. In this manner, the heads of fasteners 264 and 265 force flat workpiece 203 against flat workpiece chuck 202 when they are secured, holding it rigidly in well 268 of workpiece chuck 202.

In one embodiment, flat workpiece 203 is selected to meet the requirements of ASTM testing standard D 6079 such that it is a 10 millimeter diameter disk machined from annealed rod, having a Vickers hardness "HV30" as determined by Specification E92, a scale number of 190–210. To meet the testing specifications, the workpiece is also turned and lapped, followed by polishing to a surface finish of $R_a$ less than 0.02 micrometers.

In one embodiment, flat workpiece chuck 202 is arranged within testing chamber 201 such that flat workpiece 203 is maintained in a static position when spherical workpiece 204 is moved across it under load during a test. In such an embodiment, spherical workpiece chuck 205 is mounted on actuator rod 208. The mounting device maintains spherical workpiece 204 in a rigidly fixed relationship with the end of arm 208 that is residing within testing chamber 201. In this manner, motion imparted by actuator rod 208 to spherical workpiece chuck 205 is translated to identical motion at the contact point between spherical workpiece 204 and flat workpiece 203.

In one embodiment, spherical workpiece chuck 205 contains well 226 which is of sufficient dimension to accommodate a spherical workpiece 204 that meets the requirements of a spherical workpiece specified in ASTM Testing Standard D 6079. That testing standard specifies a spherical workpiece having a diameter of 6 millimeters and being made from ANSI E-52100 steel. Further, ASTM Testing Standard specifies that the spherical workpiece be Grade 24 per ANSI B3.12, have a Rockwell "C" scale hardness number of 58–66 as determined by test method E18, and have a surface finish $R_a$ of less than 0.05 micrometers. The well is also equipped with a fastening mechanism 298 such that spherical test workpiece 204 is maintained rigidly fixed within well 226.

Alternative arrangements regarding the orientation of flat workpiece chuck 202 and spherical workpiece chuck 205 will be obvious to one skilled in the art. Thus, spherical workpiece chuck 202 could be mounted to maintain a fixed location relative to testing chamber 201 and flat workpiece chuck mounted on actuator rod 208. In like manner, the static workpiece chuck could be disposed below the moving workpiece chuck with workpiece loading device 207 forcing the workpiece contained in its associated chuck up against the work face of the corresponding workpiece instead of down against the work face of the corresponding workpiece, as it is shown in FIG. 2. This change can be made without effecting the function, means, or result of the present invention.

Testing chamber 201 contains workpiece loading device 207. Workpiece loading device 207 supplies a contact force between workpiece surfaces during a test of the lubricating properties of a fluid placed within the testing chamber. Fixed to workpiece loading device 207 is flat workpiece holding chuck 202. During the conduct of a test, flat workpiece 203 having a surface prepared for testing is clamped in flat workpiece holding chuck 202 such that it is held immobilized in the chuck with the prepared surface facing away from workpiece loading device 207. Assembled workpiece loading device 207, flat workpiece workpiece chuck 202, and workpiece 203 are placed into testing chamber 201. The assembly is placed within testing chamber 201 such that the prepared surface of workpiece 203 is in contact with spherical workpiece 204 described above, workpiece loading device 207 providing a measured contact force between the contacting surfaces of the flat and spherical workpieces.

In the best mode, workpiece loading device 207 is a cylindrical weight of sufficient mass that under the influence of normal gravity it will apply a force of 200 g to the contact area between the surfaces of the flat workpiece 203 and spherical workpiece 204 when the workpieces are clamped into their respective chucks and the assembled workpiece loading device and flat workpiece is slid down into testing chamber 201 until contact is made between flat workpiece 203 and spherical workpiece 204. Best mode workpiece loading device 207 is machined to permit a sliding fit between the inside wall of cylindrical testing chamber 201 and the outer cylinder wall of workpiece loading device 207. In the best mode, machine tolerances are maintained to permit workpiece loading device 207 to slide within testing chamber 201 inside bore without binding or striction. In the best mode, the true of the testing chamber 201 bore and the outer surface of workpiece loading device 207 is maintained to sufficiently close tolerance that workpiece loading device 207 can slide freely but the fit is not so loose that workpiece loading device will "rock" or otherwise be displaced when differential motion is imparted to the workpieces by, with reference to FIG. 1, motion generator 111 acting on, with reference to FIG. 2, actuator rod 208 during the conduct of a test. In this manner, flat workpiece 203 is maintained in a fixed position relative to testing chamber 201 by flat workpiece chuck 202 and workpiece loading device 207 while spherical workpiece 204 is maintained in a fixed position relative to the end of actuator rod 208 fixed to spherical workpiece chuck 205 as actuator rod 208 is moved during a test.

Figure 3:
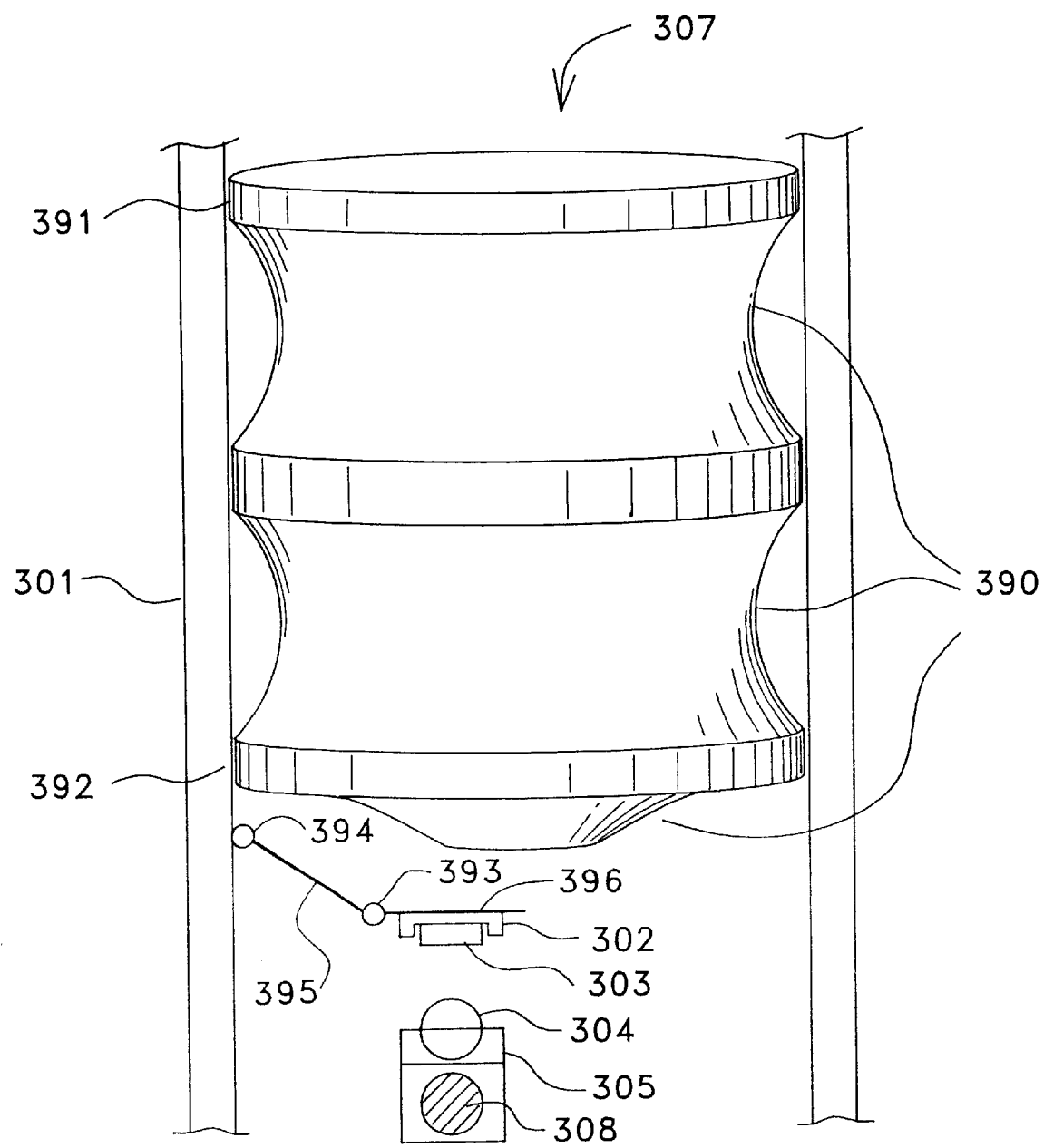
FIG. 3 is a cutaway view of a section of the testing chamber with an alternative workpiece loading device installed.

Alternative embodiments of workpiece loading device 207 will be apparent to one practiced in the art. With reference to FIG. 3, a cutaway elevation view, workpiece loading device 307, which is equivalent to workpiece loading device 207 and its equivalents, discloses an alternative embodiment of the workpiece loading device. In this embodiment the body of the workpiece loading device 307 is longer than the workpiece loading device 207 of FIG. 2 disclosed above. In addition to being longer, workpiece loading device 307 contains void sections 390 cut as groves about the circumference of the body. The additional length and voids give the longer workpiece loading device 307 the same weight as the previously disclosed workpiece loading device. The additional length of the device gives workpiece loading device 307 greater resistance to horizontal displacement, rocking, or wiggling in the bore of testing chamber 301 when actuator rod 308 imparts differential motion to workpieces 303 and 304 by virtue of the longer lever effect achieved through increasing the distance between points 391 and 392 over that used in embodiments of the workpiece loading device made from an solid cylinder such as the one disclosed above, with reference to FIG. 2, as workpiece loading device 207. These points of contact are critical in maintaining axial alignment of the workpiece loading device 307 with the testing chamber 301 bore axis. In FIG. 3, the path of motion of actuator rod 308, which is the equivalent of actuator rod 208 of FIG. 2, is in and out of the plane of FIG. 3.

An additional feature of this alternative embodiment is that by machining grooves 390 into the side of workpiece loading device 307, contact area between workpiece loading device 307 and the inside walls of testing chamber 301 is reduced. Reduced contact area provides lower sliding resistance for workpiece loading device 307 as it traverses along the inside wall of testing chamber 301.

With further reference to FIG. 3, an alternative embodiment of the workpiece loading device 307 and a flat workpiece chuck 302 is shown. In this embodiment, flat workpiece chuck 302 is hingably fixed to the side wall of testing chamber 301 such that it may be displaced along the bore of testing chamber 301, but it's motion along the axis of travel of actuator rod 308 is prevented. In this alternative embodiment, a hinge or other flexible attachment must be provided at point 393 such that flat workpiece chuck 302 will pivot under the influence of workpiece loading device 307. A pivot 393 permits a flat workpiece held in flat workpiece chuck 302 to remain tangential to a spherical workpiece it contacts as the workpiece is displaced up and down along the bore axis of testing chamber 301. Attachment of pivot arm 395 to the wall of testing chamber 301 may be made by a pivot 394 or any other type of attachment that permits displacement of the attached flat workpiece chuck 302 along testing chamber bore axis while rigidly locating flat workpiece chuck 302 relative to motion imparted to spherical workpiece chuck 305 by actuator rod 308. Examples of such embodiments will be familiar to one skilled in the art, and includes hinges, mechanical fastening of flat springs, and sliding contact of a machine element in a groove or key way machined into the inner surface of testing chamber 301. When an arrangement of machine elements utilizing sliding contact and a groove or key way machined into the wall of testing chamber 301 is employed, hingable connection 393 may be eliminated. In such an embodiment, flat workpiece chuck 302 is fastened to a sliding bar, rod, or block (not illustrated) that traverses the bore of testing chamber 301 and fits into slots spaced 180 degrees apart such that it is substantially perpendicular to the direction of travel of actuator rod 308.

Additional embodiments of workpiece loading device 307 will be apparent to one skilled in the art wherein workpiece loading device is fixed in the bore of testing chamber 301 by friction or mechanical fastener and force is applied to the contact area between the flat workpiece 303 and spherical workpiece 304 using an adjustable spring tension device that presses against flat workpiece chuck 302 on face 396. Such a workpiece loading device may be used with any embodiment of workpiece chuck devices discussed above.

With reference to FIG. 2, spherical workpiece chuck 205 is rigidly fixed to actuator rod 208 such that linear motion of actuator rod 208 does not impart deflection or rotation of spherical workpiece chuck 205 when actuator rod 208 is moved under conditions where spherical workpiece 204 and flat workpiece 203 are held in contact under load imparted by loading device 207.

Spherical workpiece chuck may be fixed to actuator rod 208 using mechanical fasteners, a combination of machine elements and mechanical fasteners, or by welding or such soldering and brazing techniques as are well known to one skilled in the art of joining metal parts. In one embodiment, spherical workpiece chuck 205 is machined to provide socket 225. In this embodiment, socket 225 is of sufficient diameter to receive actuator rod 208 with "press fit" machine tolerances such that workpiece chuck 205 socket may be mounted onto the end of actuator rod 208 by press fitting actuator rod 208 into socket 225. Alternatively, the fit may be of looser tolerance and spherical workpiece chuck 205 provided with a hole 235 bored through to intersect socket 225. When socket 225 is fitted onto actuator rod 208 holes 235 and hole 236 bored into the actuator rod 208 align. This alignment permits fastener 237 to be inserted therein, providing for a rigid fastening of spherical workpiece chuck 205 to actuator rod 208. Additional methods of attachment between spherical workpiece chuck 205 and actuator rod 208 including all manner of sockets provided on spherical workpiece chuck 205 and grooves or flats machined on actuator rod 208, with either press fit or mechanical attachment such as set screws, bolts, rivets and the like will be familiar to one skilled in the art. Just as numerous are schemes in which actuator rod 208, spherical workpiece chuck 205, or both contain plates or other fitments affixed to them such that they afford a support surface by which fitment surfaces actuator rod 208 and spherical workpiece chuck 205 may be fastened together using any mechanical fastener known in the art. Those skilled in the art will appreciate that actuator rod 208 and spherical workpiece chuck 205 may be affixed by all manner of weld, braze, and solder joint applied to all manner of socket and fitments appended to actuator rod 208 and spherical workpiece chuck 205. This is true so long as the filler material chosen to complete the weld, braze, or solder joint is sufficiently robust to withstand the conditions of the test conducted in testing chamber 201.

Figure 4:
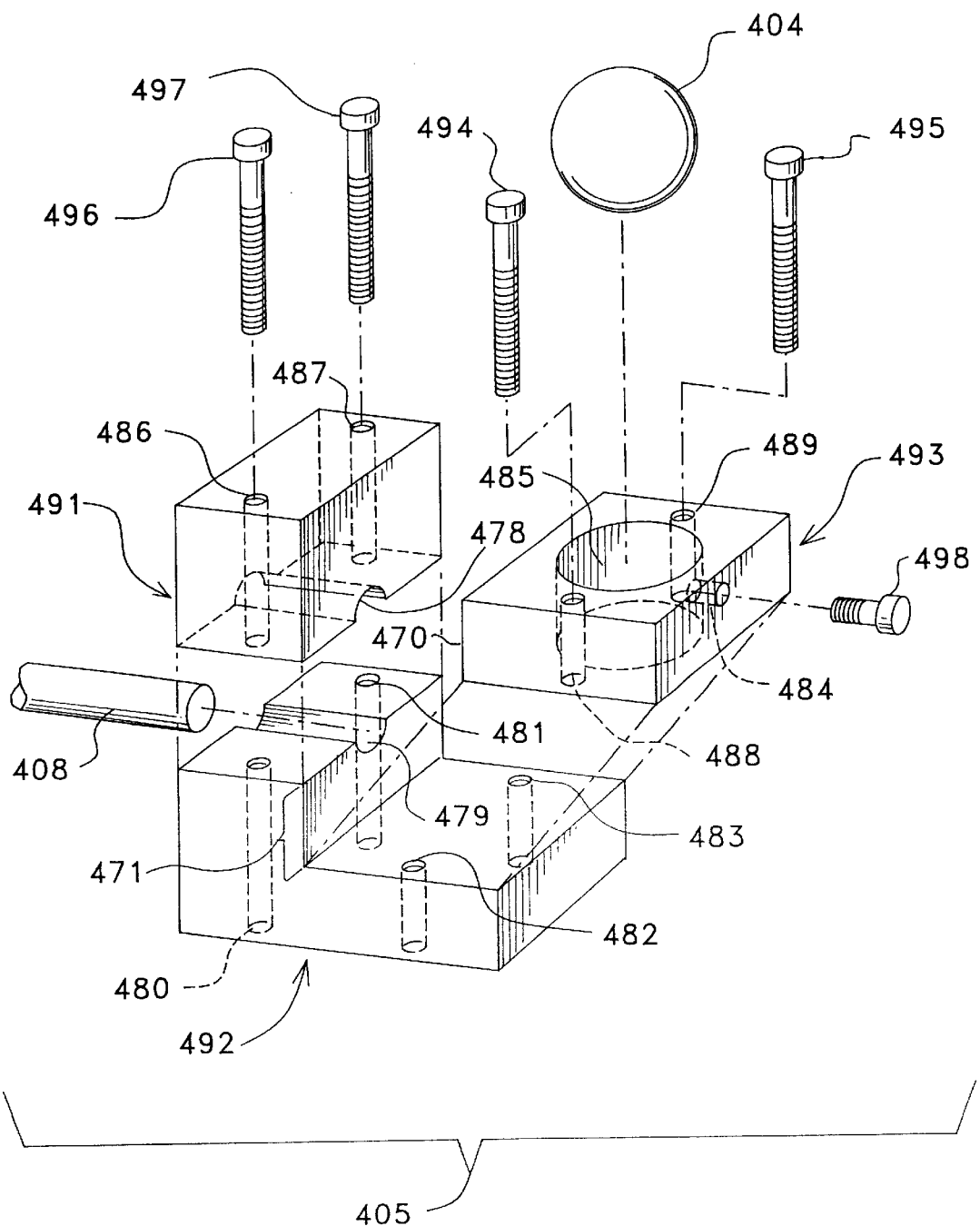
FIG. 4 is a prospective elevation of a spherical workpiece chuck and actuator rod end.

The best mode of practicing spherical workpiece chuck 205 may be understood with reference to FIG. 4. With reference to FIG. 4, spherical workpiece chuck assembly 405, which is the equivalent of spherical workpiece chuck 205 of FIG. 2 and its equivalents, is composed of 3 major components, support plate 492, clamping plate 491, and spherical workpiece holder 493. All parts of spherical workpiece chuck assembly 405 are made from material chosen such that it can withstand repeated exposure to the testing conditions obtaining in, with reference to FIG. 2, the testing chamber 201 during the conduct of a test. Spherical workpiece holder 493 comprises a block of material into which has been fashioned circular well 485. Well 485 is of sufficient diameter to admit spherical workpiece 404. Spherical workpiece 404 is the equivalent of spherical workpiece 204 of FIG. 2. The depth of circular well 485 is sufficient such that it extends above the midline of a spherical workpiece 404 inserted into it. Blind bored through one face of spherical workpiece holder 493, perpendicular to well 485 and of sufficient depth to intersect well 485 is conduit 484. Conduit 484 is of suitable dimension and wall conformation to receive mechanism 498 for securing spherical workpiece 404 within well 485. When clamped onto support plate 492, conduit 484 is oriented such that access to it is unimpeded by any feature of support plate 492. Additionally, spherical workpiece holder 493 contains bored through conduits 488 and 489. Conduits 488 and 489 are bored such that they are parallel to and centered on either side of well 485. Conduits 488 and 489 are of suitable dimension and wall finish that they are capable of receiving fasteners 494 and 495, which are suitable for fastening workpiece holder 493 to support plate 492 utilizing conduits 482 and 483 bored through support plate 492.

Support plate 492 is a block of material having an "L" shape in profile. Raised portion 471 of support plate 492 is dimensioned such that it is the same size as the bottom of clamping plate 491 which is fastened to it. Support plate 492 is provided with conduits 480, 481, 482, and 483. Conduits 480 and 481 are through bored perpendicular to and centered on either side of groove 479. Conduits 480 and 481 are of suitable dimension and surface configuration that they can receive fasteners 496 and 497 respectively. Fasteners 496 and 497 are chosen such that they are suitable for attaching clamping plate 491 to support plate 492.

Conduits 482 and 483 are bored through parallel to conduits 480 and 481, and located on support plate 492 such that they will line up with conduits 487 and 488 on spherical workpiece holder 493 when spherical workpiece holder 493 is placed on support plate 491. In this manner, conduits 482 and 483 serve to facilitate fastening spherical workpiece holder 493 to support plate 491.

Clamping plate 491 is a block of material with conduits 486 and 487 bored through it such that they align with conduits 480 and 481 of support plate 492 when clamping plate 491 is placed on support plate 492. Additionally, groove 478 is machined into clamping plate 492 such that it is perpendicular to and centered between conduits 486 and 487. Conduits 486 and 487 are of suitable dimension and surface finish that they can receive a fasteners 496 and 497 which are chosen to facilitate attaching clamping plate 491 to support plate 492.

With further reference to FIG. 4, grooves 478 and 479 are disposed on clamping plate 491 and support plate 492, and dimensioned such that when clamping plate 491 and support plate 492 are fastened together they form a socket within which actuator rod 408, which is equivalent to actuator rod 208 of FIG. 2 and its equivalents disclosed elsewhere in this document, can be placed. Grooves 479 and 478 are dimensioned such that they provide snug or press fit between the outer diameter of actuator rod 408 and the walls of grooves 478 and 479 when actuator rod 408 is placed into grooves 478 and 479.

The depth of grooves 478 and 479 is such that when actuator rod 408 is place within either groove, up to one-half of the diameter of actuator rod 408 is contained within the groove. When fasteners 496 and 497 are employed to fasten clamping plate 491 to support plate 492 with actuator rod 408 disposed within grooves 478 and 479, support plate 492 is thereby rigidly fixed to actuator rod 408. Thus, the assembly of support plate 492 with clamping plate 491 and spherical workpiece chuck 493 provides a method of rigidly fastening spherical workpiece 404 to actuator rod 408.

With further reference to FIG. 4, grooves 478 and 479 are fashioned into clamping plate 491 and support plate 492 respectively. They are dimensioned such that they may receive the end of actuator rod 408 with snug or press fit between the outer diameter of actuator rod 408 and the walls of grooves 478 and 479. The dimensions of grooves 478 and 479 taken together are such that when actuator rod 408 is placed within said grooves, and support plate 492 is fastened to clamping plate 491, there is sufficient clearance between support plate 492 and clamping plate 491 that securing fasteners 496 and 497 exerts sufficient clamping force on actuator rod 408 that support plate 492 is rigidly fixed to actuator rod 408. With further reference to FIG. 4, in the best mode, fasteners 498, 497, 496, 495, and 494 are machine screws. Conduits 480, 481, 482, 483 and 484 have thread grooves in their walls of suitable configuration to permit fasteners 494, 495, 496, 497, and 498 to thread into them. In other embodiments, where machine screws are employed as fasteners, one of the pairs of conduits through which each passes contains a bore of sufficient diameter to permit sliding fit between the screw and the conduit, while the corresponding conduit in the other piece has threaded walls into which the machine screw can be threaded. Thus, for example, fastener 494 may pass through conduit 488 in spherical workpiece holder 493 and thread into corresponding conduit 482 of support plate 492, or it may pass through conduit 482 and thread into conduit 488. Alternatively, by way of example, conduits 482 and 488 may both have bores large enough to permit fastener 494 to pass through, and a separate fastener part, in the case of a machine screw a threaded nut, may be employed to secure the fastener. As for the example using conduits 482 and 488 and fastener 494, these permutations are equally possible for all other pairs of conduits and related fasteners recited above.

Although machine screws were used as examples of one embodiment of fasteners suitable for fastening the various components of the testing apparatus, fasteners 494, 495, 496, 497, and 498 may be bolts, quarter turn fasteners, cam lock fasteners, and such like as will be familiar to one skilled in the art.

Additional features of testing chamber 201 are disclosed with reference to FIG. 2. Testing chamber 201, which is the equivalent of testing chamber 101 of FIG. 1 and its equivalents disclosed elsewhere in this document is constructed with wall thickness and sealing methodology such that it can contain pressures exceeding 200 psi, but testing chamber 201 is provided with thin wall section 213 (which is the equivalent of blow out panel 113 of FIG. 1) in its bottom. Thin wall section 228 is constructed such that in the event that there is a catastrophic overpressure condition within chamber 201, it will fail before any other structural element of assembled testing chamber. This is to say that cap 206, testing chamber 201, and the seal between cap 206 and testing chamber 201 are sufficiently robust that they will withstand pressure excursions sufficient to fail thin wall section 213 of testing chamber 201. In addition, all conduit fittings, such as the fittings associated with conduits 221, 222, 223, and 224 as well as the seal 232 of actuator rod support arm will also withstand pressure excursions sufficient to fail blow out panel 213.

With reference to FIG. 2, the best mode of constructing thin wall section 213 is disclosed. In one embodiment of testing chamber 201, testing chamber 201 is constructed from a cylindrical billet of material, the chamber being formed by blind boring well 214 into the billet. The diameter of well 214 is chosen to leave sufficient side wall thickness 230 for the finished testing chamber side walls to withstand overpressure conditions. The depth 227 of well 214 is chosen to provide end wall thickness 228 which is ¼ the thickness of the next thinnest section of testing chamber 201. To further insure preferential failure of the thin section of testing chamber 201 in the event of an drastic overpressure condition occurring with the chamber, circular groove 229 is machined into the thin portion of the bottom wall of testing chamber 201. The depth of groove 229 is selected to give a wall thickness in the bottom of the groove that is about one half the wall thickness of the thin wall section 228 of testing chamber 201. Taken together, thin wall area 228 and circular groove 229 form blow out panel 213. Groove 229 provides a construction such that the bottom of testing chamber 201 will tear along the groove about its circumference if the blow out panel 213 flexes outward sufficiently. Such flexure and tearing will occur if a sufficiently high pressure excursion occurs within chamber 201 such as would accompany an explosion or rapid combustion of a lubricant sample contained within testing chamber 201.

Other embodiments of blow out panel 213 will be obvious to one skilled in the art. For example, the blow out panel could be formed as a separate member, a groove machined into a circular disk of the proper thickness, which is then welded to one end of an open hollow cylinder to form the testing chamber of the above description. Other embodiments in which a fitment is provided in the end of testing chamber 201 such that it can secure a frangible disk that fails above a selected pressure will also serve to effect blow out panel 213. Those skilled in the art of handling high pressure fluids will be aware of other embodiments which are standards of the industry for relieving potentially catastrophic over pressure conditions from sealed vessels in a controlled manner.

With further reference to FIG. 2, actuator rod support arm 210, which has a first end appended to testing chamber 201 and a second end open to the ambient environment may be formed from a monolithic block of material. In such a case, testing chamber 201 and actuator rod support arm 210 are machined as one unit. An identical monolithic unit may be formed using casting techniques such as are well known, machining the raw casting to achieve the close tolerance required in the finished unit. Testing chamber 201 and actuator rod support arm 210 may also be formed as separate units by any combination of machining and metal forming techniques which are well known and then joined by any method such as are well know to those practiced in the art.

Examples of methods contemplated for joining a separate actuator rod support arm 210 and testing chamber 201, but not meant to be an exclusive or comprehensive list of joining methods contemplated, for various embodiments are welding, a flange and gasket or packing connection, and a threaded fitment. The latter example is shown in FIG. 2. In this example threaded grooves are placed on the outside of one end of actuator rod support arm 210 such that it may be threaded into a receiver containing complimentary thread groves machined into the side of testing chamber 201. Other such joining schemes will be obvious to one practiced in the art. When a threaded fitment is used to join actuator rod support arm 210 to testing chamber 201, an o-ring or other gasket material 232 is inserted between the two pieces to effect sealing. The material used and the surfaces against which the o-ring or gasket effect a seal are selected appropriate to the pressure and chemical nature of fluids contained in testing chamber 201 during a test.

With further reference to FIG. 2, actuator rod 208 passes through actuator rod support arm 210. Actuator rod support arm 210 acts as a support, guide, and bearing for actuator rod 208 as well as a method of sealing testing chamber 201 from the ambient environment.

With reference to FIG. 2, conduit 270, which is appended to actuator rod support arm 210 serves to conduct fluid into annular space 231 between the inner diameter of actuator rod support arm 210 and the outer diameter of actuator rod 208. During a test, annular space 231 is flushed with nitrogen gas supplied to the space by conduit 270 appended to actuator rod support arm 210. The gas passing into annular space 231 passes along the annular space traveling away from testing chamber 201 toward the open end 233 of actuator rod support arm 210. In this manner annular space 231 purge gas reaches the ambient environment surrounding actuator rod support arm 210. The outside diameter of actuator shaft 208 and the inside diameter of actuator rod support arm 210 are machined to close tolerance. To minimize binding and striction as actuator rod 208 passes along actuator rod support arm 210 the true of both the bore in actuator rod support arm 210 and the shaft comprising actuator rod 208 is also maintained to a low incidence of deviation. The combination of the small clearance between actuator rod 208 and the bore in actuator rod support arm 210 together with the low deviation from linearity of the actuator rod 208 and the bore through actuator rod support arm 210 provides an assembly wherein a pressure gradient exceeding 200 psi can be maintained in annular space 271 between conduit 270 and opening 233 of actuator rod support arm 210 when actuator rod 208 is in place, whilst actuator rod 208 moves freely in the bore. In this manner, fluid under pressure residing in testing chamber 201 may be contained without the load of a mechanical seal impinging on actuator rod 208. In one embodiment of the present invention, the clearance between the inside diameter of the bore through actuator rod support arm 210 and the outside diameter of the shaft comprising actuator rod 208 is 50 microns, with the true of the bore and shaft held to a deviation of less than 100 microns.

Other embodiments are possible in a which sealing elements such as o-rings are disposed along actuator rod 208, held in place by grooves machined into the inner surface of the bore in actuator rod support arm 210, or seated in grooves machined into actuator rod 208. Such sealing devices could be used alone or in conjunction with gas pressure introduced via conduit 270 into the annular space 231 to prevent fluid contained at high pressure in testing chamber 201 from being forced past such sealing devices. Sealing of shafts and other mechanical actuators against high pressure fluid containment is well known in the art. Sealing elements such as o-rings and packing are but two examples of the sealing elements which could be employed as sealing elements. Many different construction materials and techniques for sealing actuator rod 208 to actuator rod support arm 210 will be readily apparent to one skilled in the art and may be substituted with equal effectiveness. Mechanical sealing devices are not preferred, however. Mechanical sealing devices are subject to chemical attack, mechanical degradation, and impart drag and load to the actuator rod which can effect the precision of the motion imparted to the workpieces contained in the testing chamber via the actuator rod.

The best mode of sealing actuator rod 208 to the bore through the actuator rod support arm 210 is the use of precise clearances and high pressure gas disclosed above. The advantage of the best mode in using a differential pressure gas flow to effect sealing and act as a bearing element are that fire hazard is reduced because of the diluting effect of the purge gas in the event of leakage along annular space 231. Additionally, wear of the sealing element is eliminated, effecting simpler equipment setup and maintenance. And finally, problems arising from the chemical nature of the lubricant composition undergoing test being incompatible with the seal or packing materials used to seal the testing chamber is eliminated. The preferred manner of constructing actuator rod 208 and actuator rod support arm 210 is to use the plunger and barrel of a commercially available diesel fuel injector unit. Further features of the modifications are disclosed below. An example of a commercially available fuel injector unit having a suitable barrel and plunger is a commercial unit manufactured by Cummins Engine Company and contains all the fitments and conduits necessary to be used in the subject testing apparatus as received.

With further reference to FIG. 1, actuator rod 108 is pivotally fixed to motion generator 111. The components of motion generator 111 are selected such that in operation motion generator 111 moves actuator rod 108 linearly along the bore of actuator rod support arm 110 at a constant frequency. The rate of travel of actuator rod 108 while under the influence of motion generator 111 preferentially follows a sinusoidal function under all conditions of load, however other displacement functions may also be employed. The best mode motion generator 111 comprises an eccentric element mounted on a shaft coupled to a constant speed electric motor of sufficient power that it can maintain a selected rpm under all load conditions. The eccentric element is further pivotally coupled to actuator rod 108 by a crank arm capable of translating the motion of the eccentric element about the shaft into linear oscillating motion in actuator rod 108.

Figure 5:
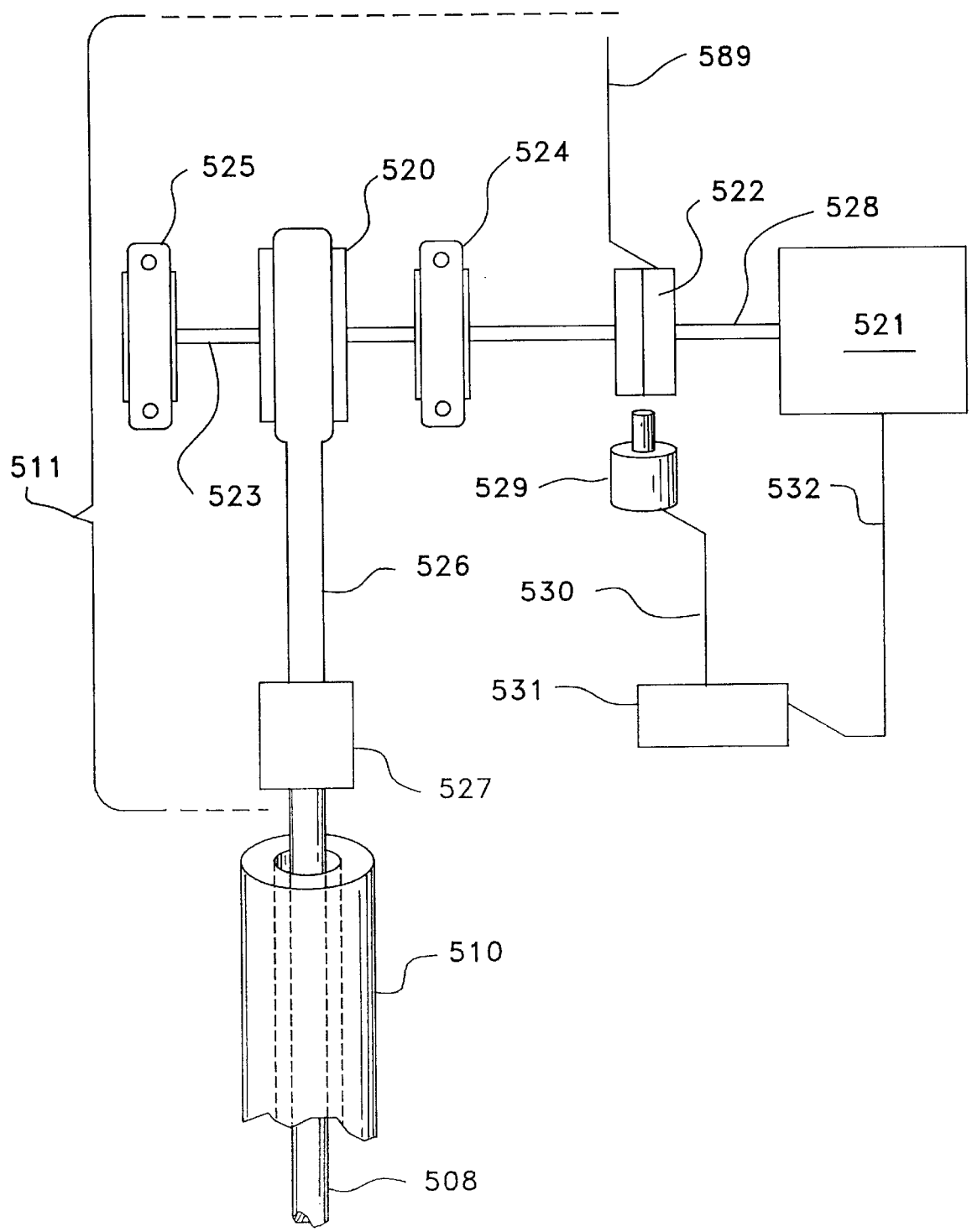
FIG. 5 is a schematic diagram of the motion generator and its attachment to an actuator rod.

Further features of motion generator 111 are disclosed in FIG. 5. With reference to FIG. 5, motion generator 511, which is equivalent to motion generator 111 of FIG. 1 and its equivalents disclosed elsewhere in this document, is comprised of electric motor 521, drive shaft 523 coupling 522, crank arm 526, pivot connector 527 cranking assembly 520 and drive shaft support bearings 524 and 525. Output shaft 528 of motor 521 is coupled to drive shaft 523 via coupling 522. Coupling 522 can be a clutch type device that permits output shaft 528 and drive shaft 523 to be coupled or decoupled in response to an electric signal applied to control line 589. Control line 589 is equivalent to control line 189 of FIG. 1.

The partial sections of actuator rod 508 and actuator rod support arm 510 shown in FIG. 5 are equivalent to, with reference to FIG. 2, of actuator rod 208 and actuator rod support arm 210 respectively and their respective equivalents disclosed elsewhere in this document. While some embodiments of the present invention have an electrically actuated hydraulic or electromagnetic clutch type device for ease of operation, any device familiar to one skilled in the art for coupling the output shaft of an electric motor to a drive shaft may be used. Coupling 522 is preferentially a simple mechanical coupling which permits coupling of output shaft 528 to drive shaft 523 with no slippage or loss of rotary motion. In embodiments using devices that permanently couple output shaft 528 to drive shaft 523, motion is commenced by applying power to electric motor 521 and ceased by disconnecting power from electric motor 521 rather than controlling the operation of drive shaft 523 by operation of a clutch/brake coupling 522.

With further reference to FIG. 5, drive shaft 523 is supported and located relative to the open end of the actuator rod support arm 510 by bearings 524 and 525.

With further reference to FIG. 5, one end of crank arm 526 is pivotally fastened to drive shaft 523 by means of cranking assembly 520. The other end of crank arm 526 is pivotally fastened to clamping assembly 527. Clamping assembly 527 in turn is fitted with a rigid clamp whereby it is rigidly fastened to the end of actuator rod 508 residing in the ambient environment.

Figure 6:
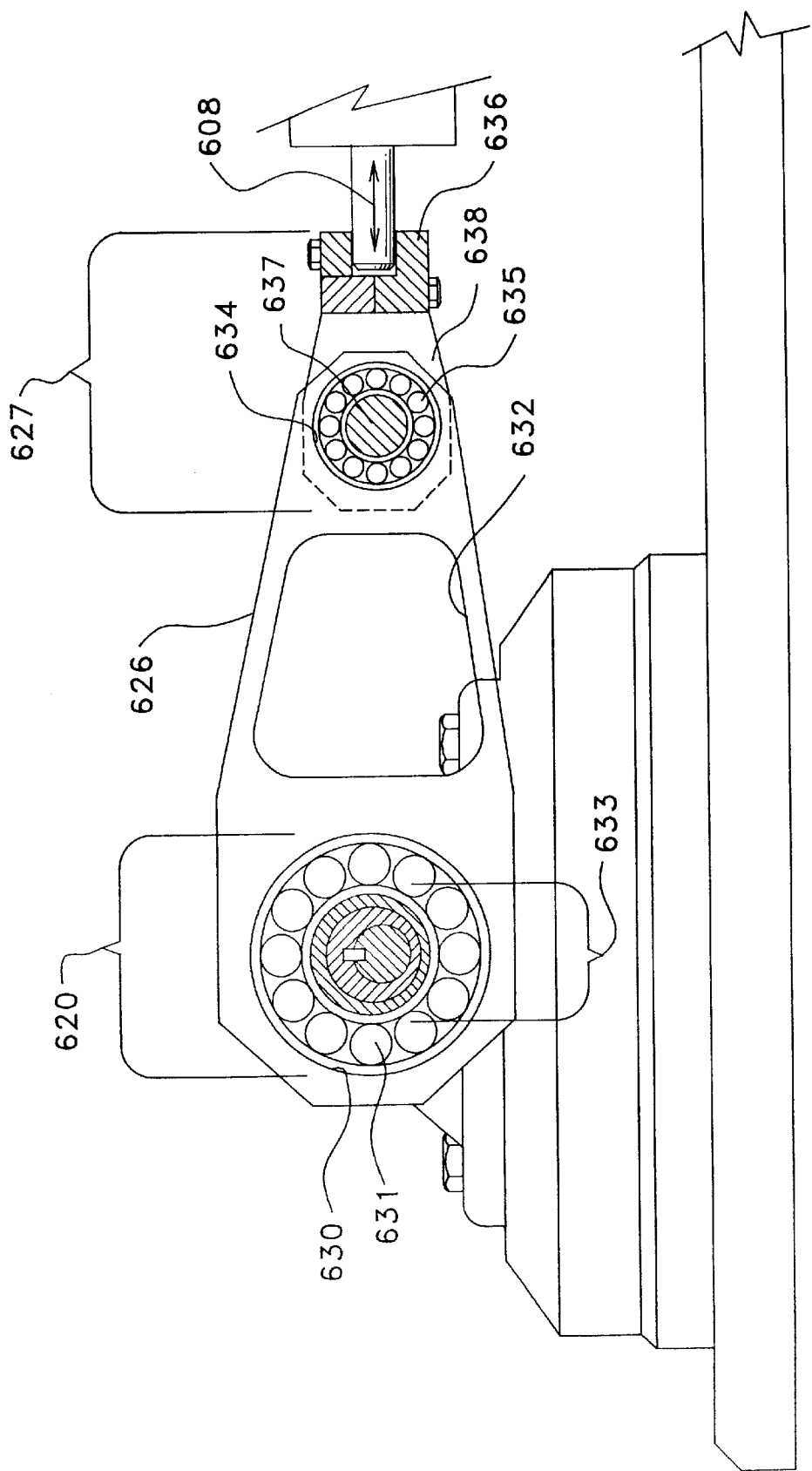
FIG. 6 is an elevation cutaway view of an embodiment of the motion generator.

Further details of best mode crank arm 526 are disclosed in FIG. 6. FIG. 6 is a partial cutaway elevation view of one embodiment of the present invention. Crank arm 626, which is the equivalent of crank arm 526 of FIG. 5, is fashioned from a rectangular beam of material. Crank arm 626 has a first end which contains hole 630. Hole 630 is of sufficient diameter to mount bearing assembly 631. Bearing assembly 631 may be secured by any mean familiar to one skilled in the art, examples of which are given without meaning to serve as an exhaustive list of possibilities, said examples being press fit, set screw, and cinch clamp construction. Crank arm 626 has a second end which contains hole 634. Hole 634 is of sufficient diameter to contain bearing assembly 635. In some embodiments, voids such as void 632 are machined into crank arm 626 to reduce the mass of the crank arm.

With further reference to FIG. 6, rotation axis adjuster 633 is contained within bearing 631, and rotation axis adjuster together with bearing 631 comprise cranking assembly 620. Cranking assembly 620 is equivalent to eccentric assembly 520 of FIG. 5, and its equivalents disclosed elsewhere in this document.

With reference to FIG. 5, pivot connector 527 attaches pivotally to crank arm 526 and rigidly to actuator arm 508. The two ends of pivot connector 527 are further disclosed, with reference to FIG. 6, as actuator rod clamp assembly 627. Actuator rod clamp assembly 627 contains U-shaped portion having legs 638 (one half of the actuator clamp assembly 627 is cutaway in FIG. 6 with only one leg of the clamp assembly therefore appearing) which surrounds the end of crank arm 626. Shaft 637 passes through holes in the actuator rod clamp assembly legs 638 and through bearing 635. The ends of shaft 637 may be secured to the actuator rod clamp assembly legs 638 using set screws, press fit, snap rings and other spring in groove type compression fasteners and the like such as are well known in the art.

Figure 7:
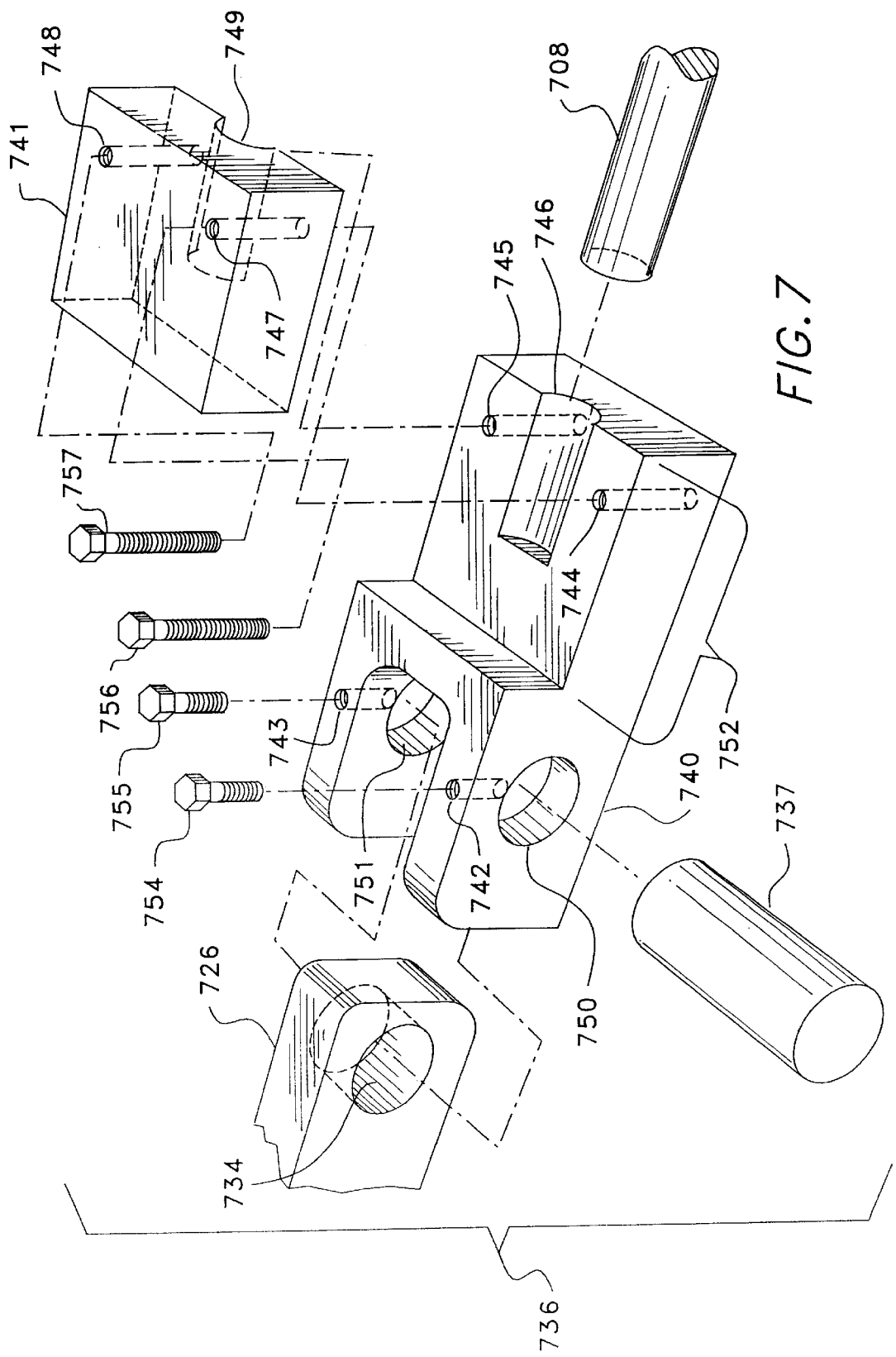
FIG. 7 is an elevation prospective view of a crank arm clamping assembly.

With further reference to FIG. 6, actuator rod clamp assembly also contains clamp portion 636 for rigidly fastening the actuator rod 608. The details of this fastening device are disclosed, with reference to FIG. 7, as actuator rod clamping assembly 736. In FIG. 7, actuator rod 708 is equivalent to actuator rod 208 of FIG. 2 and its equivalents disclosed elsewhere in this document FIG. 7 is a perspective view of one embodiment of the actuator rod clamping assembly. With reference to FIG. 7, actuator rod clamping assembly 736 consists of two pieces, swivel mount 740 and actuator rod clamp plate 741. Swivel mount 740 is made from a block of material and has a U-shaped section containing openings 750 and 751. Openings 750 and 751 are of suitable diameter to accommodate shaft 737 (which is the equivalent of shaft 637 of FIG. 6). Conduits 742 and 743 are bored perpendicular to openings 750 and 751 respectively such that conduit 743 intersects opening 751 and conduit 742 intersects opening 750. Conduits 742 and 743 have surface features suitable to receive fasteners 754 and 755 respectively. Fasteners 754 and 755 are employed to secure shaft 737 when it has been passed through bearing 758 in crank arm 726 residing between the legs of swivel mount 740 and inserted into openings 750 and 751. Crank arm 726 is equivalent to crank arm 626 of FIG. 6, and its equivalents disclosed elsewhere in this document. Bearing 758 is the equivalent of bearing 635 of FIG. 6. Fasteners 754 and 755 may be machine screws, set screws, quarter turn fasteners, cam lock fasteners and the like such as are well known.

With further reference to FIG. 7, actuator rod clamp plate 741 is a rectangular plate dimensioned to fit notch 752 machined into swivel mount 740. Swivel mount 740 contains bored through conduits 744 and 745. These conduits are parallel to conduits 742 and 743 and centered on either side of groove 746 in the notched section 752 of swivel mount 740. Conduits 744 and 745 are disposed on notch 752 to align with conduits 747 and 748 in actuator rod clamp 741 when the clamp plate is placed upon notch 752. When actuator rod clamp plate 741 is placed on notch 752 it may be fastened by means of fasteners 756 and 757 inserted through conduits 747 and 748 respectively and thence into conduits 744 and 745 in swivel mount 740.

Centered between conduits 744 and 745 is groove 746. Groove 746 is dimensioned to accommodate the outer diameter of actuator rod 708, which is the equivalent to actuator rod 608 of FIG. 6 and its equivalents disclosed elsewhere in this document.

With further reference to FIG. 7, actuator rod clamp 741 contains groove 749, dimensioned to accommodate the outer diameter of actuator rod 708. Conduits 748 and 749 are through bored perpendicular to and centered on either side of groove 749. When actuator rod clamp 741 is fastened to swivel mount 740 while actuator rod 708 is disposed between grooves 746 and 749, actuator rod 708 is rigidly secured to the assembled actuator rod swivel clamp 736.

All tolerances and elements of actuator rod swivel clamp assembly 736 are controlled such that the finished assembly transmits all lateral displacement imparted by, with reference to FIG. 6, rotation axis adjuster 633 to actuator rod 608, without lateral motion being lost to displacement from flexure or compression of the mechanical elements employed in the assembly.

Figure 9:
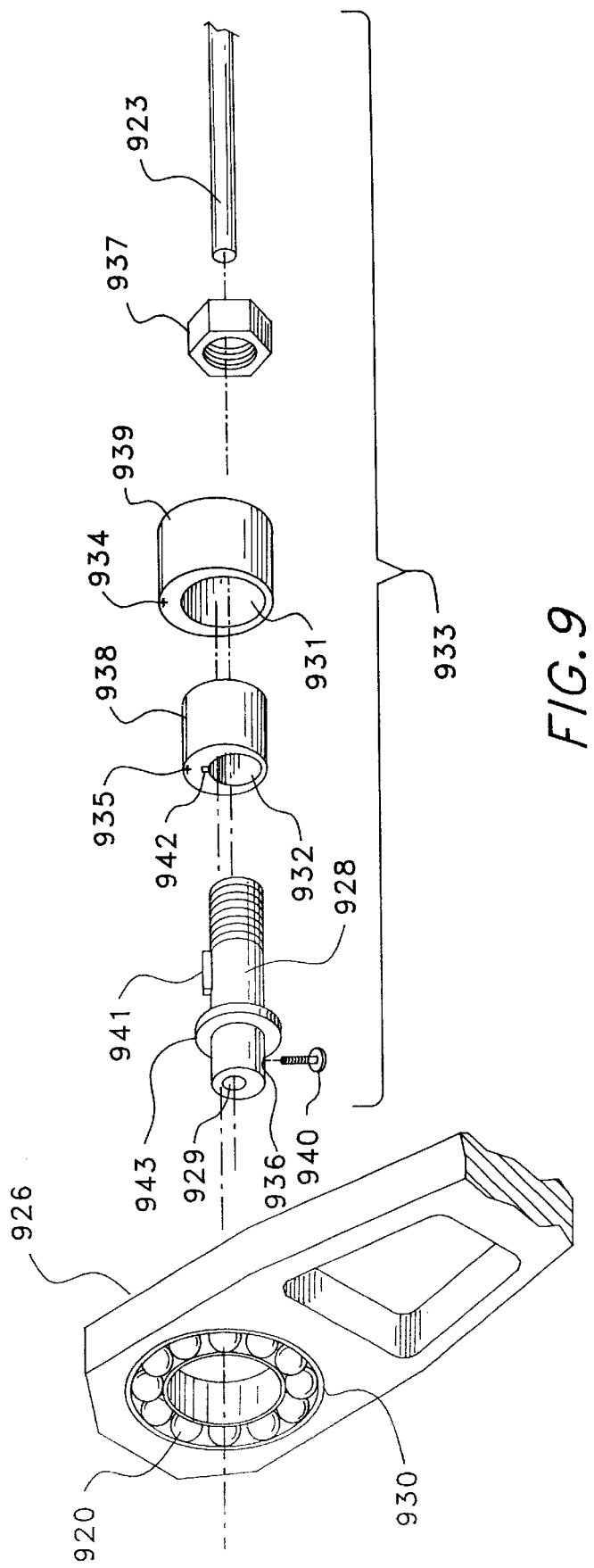
FIG. 9 is a perspective view of an embodiment of the rotation axis adjuster.

With reference to FIG. 9, rotation axis adjuster 933, which is the same as rotation axis adjuster 633 of FIG. 6, is comprised of two nesting eccentric collars, 938 and 939 mounted on eccentric locking shaft 928. Eccentric locking shaft 928 has centered bored through hole 929, which is of sufficient diameter to admit drive shaft 923. Drive shaft 923 is equivalent to drive shaft 523 of FIG. 5 and its equivalents disclosed elsewhere in this document. Once drive shaft 923 is located within hole 929, eccentric locking shaft 928 is secured to drive shaft 923 by set screw 940. It will be obvious to one skilled in the art that numerous other schemes for securing eccentric locking shaft 928 to drive shaft 923 may be equally well employed. Eccentric locking shaft 928 bears keyway 941, which together with a shaft key (not shown) and keyway 942 fashioned into eccentric collar 938 acts to lock eccentric collar 938 to eccentric locking shaft 928.

With further reference to FIG. 9, eccentric collar 938 is cylindrical in form and contains through bored hole 932 parallel to the cylinder major axis, but placed off center by an amount that is one quarter of the maximum displacement desired for actuator rod 908, which is equivalent to actuator rod 608 of FIG. 6 and its equivalents disclosed elsewhere in this document. Through bored hole 932 is of sufficient diameter to accommodate eccentric locking shaft 928.

With further reference to FIG. 9, eccentric collar 939 is cylindrical in form and contains through bored hole 931 parallel to the cylinder major axis, but placed off center by an amount that is one quarter of the maximum displacement desired for actuator rod 908. Through bored hole 931 is of sufficient diameter to accommodate eccentric collar 938. The outer diameter of eccentric collar 939 is sized to fit within bearing assembly 930, which is equivalent to bearing assembly 630 of FIG. 6.

With further reference to FIG. 9, when eccentric collar 938 is inserted into hole 931 of eccentric collar 939, and eccentric locking shaft 928 has been located within hole 932 of eccentric collar 938, the eccentric collars can be locked together by forcing them against the edge of circular lip 941 machined into eccentric locking shaft 928 using locking fastener 937. In use, the nested eccentric collars are rotated to give the desired displacement to shaft 908 prior to being locked in place on eccentric locking shaft 928 using locking fastener 937. In the best mode locking fastener 937 is a nut that threads onto bolt threads machined into the end of eccentric locking shaft 928, but one skilled in the art will appreciate that there are numerous other devices which can also be employed to lock eccentric collars 938 and 939 in place.

With further reference to FIG. 9 adjustment of stoke length of actuator rod 908 by rotation of eccentric collars 938 and 939 will be explained. When eccentric collars 938 and 939 are rotated so that points 935 and 934 are 180 degrees apart, rotation of the assembly about a shaft running through hole 932 will result in concentric tracking of the outside surface of eccentric collar 939 since the centerline offset of hole 932 in the inner eccentric collar (938) is exactly offset by the centerline offset of hole 931 in the outer eccentric collar (939). The net effect is no displacement perpendicular from the axis of rotation. When points 934 and. 935 are rotated so that they lie 0 degrees apart, rotation of the assembly about a shaft running through hole 932 will result in the maximum eccentric tracking of the outside surface of eccentric collar 939 available from the assembly. This is because the centerline offset of hole 932 in the inner eccentric collar (938) adds to the centerline offset of hole 931 in the outer eccentric collar (939). The net effect is that when eccentric collars 938 and 939 are aligned for maximum displacement, measuring from a fixed point perpendicular to the axis of rotation of drive shaft 923, there will be lateral variation of the location of the surface of collar 939 that is twice the sum of the distance by which holes 932 and 931 have been bored off center.

Other embodiments of the rotation axis adjuster are possible that are based on an adjustable crank shaft assembly. This is best understood with reference to FIG. 13. Adjustable crankshaft assembly 1300 is comprised of main shaft halves 1301 and 1302, eccentric shaft supports 1303 and 1304, and eccentric shaft 1307. Main shaft halves 1301 and 1302 are maintained in a collinear orientation with a common axis of rotation by support bearings which are not illustrated. Main shaft halves 1301 and 1302 serve the same purpose as, with reference to FIG. 9, drive shaft 923 of the double eccentric rotation axis adjuster.

Figure 13:
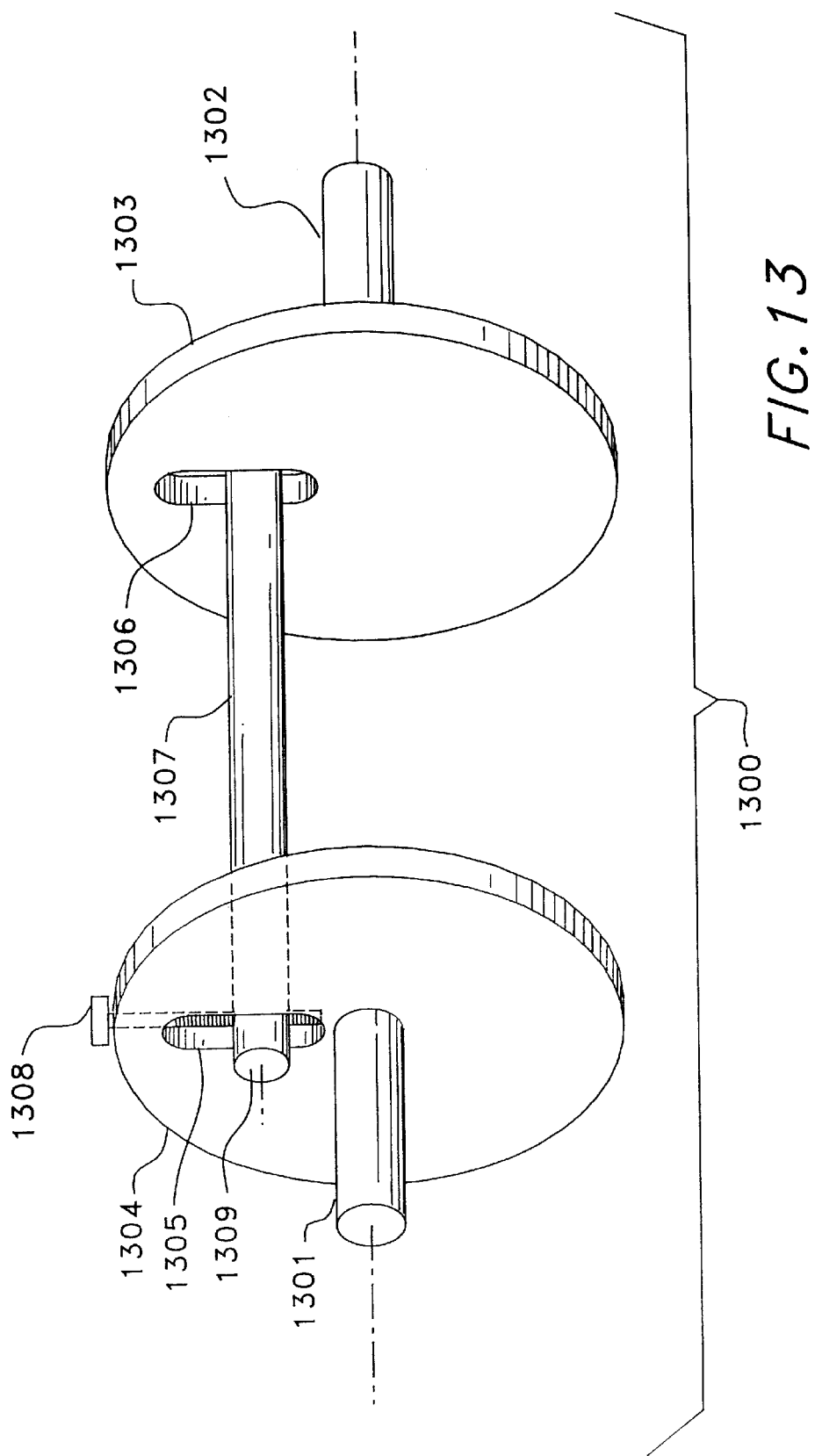
FIG. 13 is a plan view of an alternative embodiment of the rotation axis adjuster.

With further reference to FIG. 13, main shaft halves 1301 and 1302 are fastened to the center of eccentric shaft supports 1303 and 1304. Eccentric shaft supports may be in the form of a disk or a crank arm extending perpendicular from the rotational axis of the main shaft halves.

Eccentric shaft supports 1304 and 1303 have slots 1305 and 1306 respectively machined into them. Slots 1305 and 1306 are maintained parallel to each other and run perpendicular to the axis of rotation of main shaft halves 1301 and 1302.

With further reference to FIG. 13, eccentric shaft 1307 resides in grooves 1305 and 1306. It may be positioned at any point along said grooves such that it remains parallel to the axis of rotation of main shaft halves 1301 and 1302. Eccentric shaft 1307 may be located in the grooves in which it resides using a screw adjuster such as 1308 which passes the length of the groove and is threaded through end 1309 of the eccentric shaft residing in the groove, or it may be located by a shim stack or such like as will be obvious to one skilled in the art. Eccentric shaft 1307 may also be located in the slots in which it resides by using a set screw threaded into the eccentric shaft and impinging on some portion of the side wall of the slot. Variation of the stroke length imparted by the eccentric shaft is made by sliding the eccentric shaft closer to the axis of rotation of main shaft halves 1301 and 1302 to shorten the stroke, and further away from the axis of rotation to lengthen the stroke.

Figure 8:
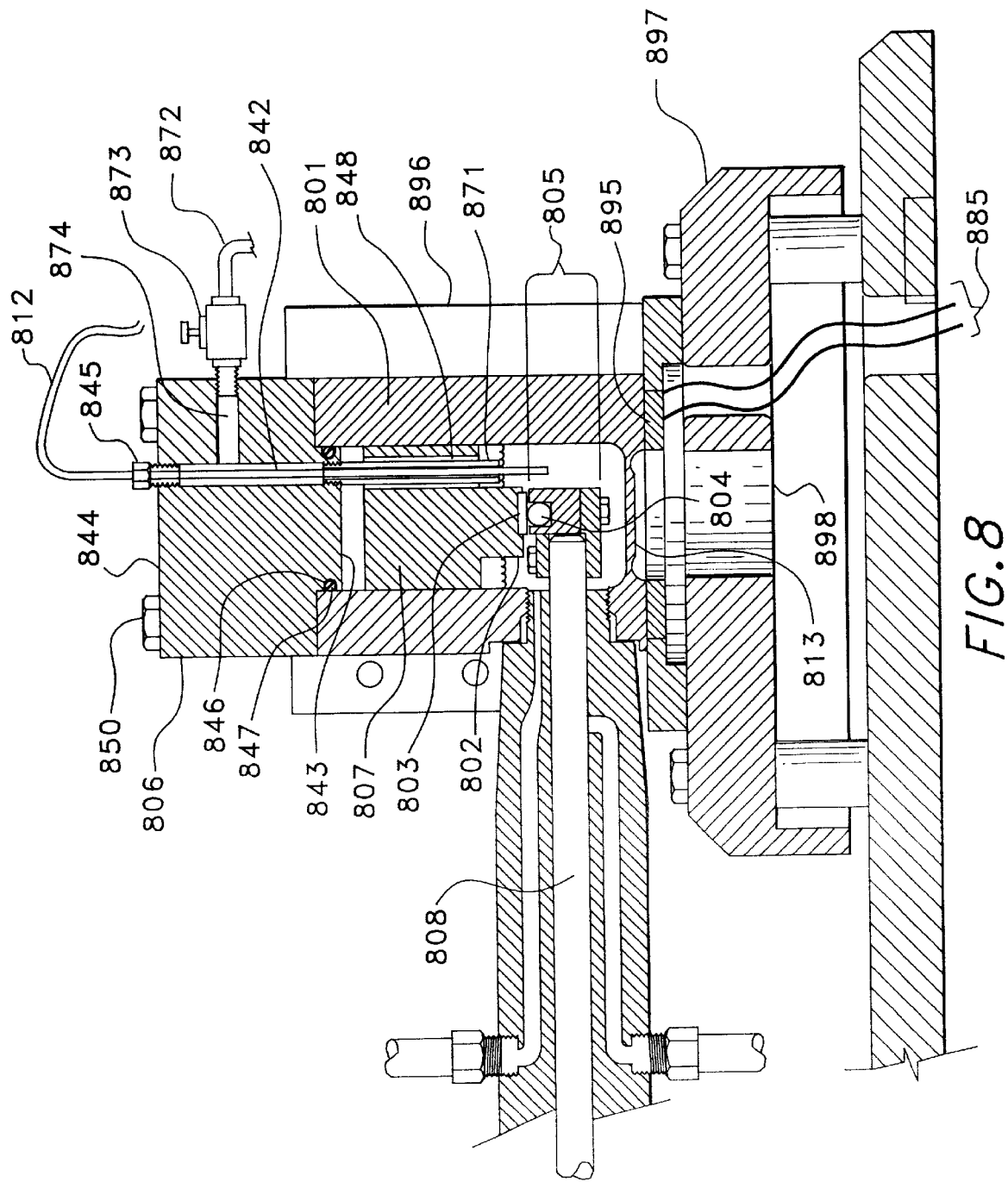
FIG. 8 is a cutaway elevation view of an embodiment of the testing chamber, actuator rod support arm and actuator rod.

With reference to FIG. 1, the level of a fluid contained within testing chamber 101 is controlled using fluid eductor tube 171. Further features of the fluid level control system can be further explained with reference to FIG. 8. With reference to FIG. 8, fluid level eductor tube 871 is fitted into through bored conduit 842 in face 843 of cap 806. Eductor tube 871 is equivalent to eductor tube 171 of FIG. 1 and its equivalents disclosed elsewhere in this document. Testing chamber 801 is equivalent to testing chamber 101 of FIG. 1 and its equivalents disclosed elsewhere in this document. Through bore hole 842 is sealed on face 844 of cap 806 by feed through fitting 845, which also seals temperature sensing device 812 to cap 806. Temperature sensing device 812 is equivalent to temperature sensing device 112 of FIG. 1 and its equivalents disclosed elsewhere in this document. Cap 806 is equivalent to cap 106 of FIG. 1 and its equivalents disclosed elsewhere in this document.

Feed through fitting 845 may be any fitting suitable to the pressure requirements of testing chamber 801 that permits sealing of a tubular member, such as thermocouple 812, with a threaded member, such as fitting 845. Examples of such fittings are, but are not limited to, compression fittings and cone or ferrule and nut fittings. It will be apparent to one skilled in the art that numerous other fittings commonly used to seal pressurized vessels may be equally well employed. In the example disclosed in FIG. 8, temperature sensing device 812 is placed coaxially in eductor tube 871, but is much smaller in diameter and so does not represent any significant impediment to fluids passing through eductor tube 871.

With further reference to FIG. 8, blind hole 874 which is bored more or less perpendicular to through bored hole 842 in cap 806 such that it intersects through bored hole 842. Blind hole 874 is the equivalent of conduit 174 of FIG. 1 and its equivalents disclosed elsewhere in this document. Attached to blind hole 874 is valve 873. Valve 873 is the equivalent to valve 173 of FIG. 1. When valve 873 is opened, fluid is vented from testing chamber 801 into a suitable receptacle, not shown, via conduit 872 fixed to valve 873. Conduit 872 is the equivalent of conduit 172 of FIG. 1 and its equivalents disclosed elsewhere in this document.

With further reference to FIG. 8, eductor tube 871 is of a length sufficient to extend from face 843 of cap 806, through conduit 848 throughbored in workpiece loading device 807 to a level just above the point of contact between workpieces held in flat workpiece chuck 802 and spherical workpiece chuck 805. Workpiece loading device 807 is the equivalent of workpiece loading device 107 of FIG. 1 and its equivalents disclosed elsewhere in this document Spherical workpiece chuck 805 and flat workpiece chuck 802 are the equivalent of, with reference to FIG. 2, spherical workpiece chuck 205 and flat workpiece chuck 202 respectively and their respective equivalents disclosed elsewhere.

To adjust the fluid level in testing chamber 801 after testing chamber 801 has been sealed and charged with a lubricant media condensate and pressurized, valve 873 is opened. The pressure contained in the testing chamber will force condensate up eductor tube 871 and through conduit 874 until it passes through valve 873. When the condensate level has dropped to below the eductor tube, gas and vapor phase material will pass through the eductor tube, but no more condensate will be removed if valve 873 remains open. In this manner, the level of condensate in the testing chamber can be adjusted after it has been heated. With further reference to FIG. 8, eductor tube 871 can be sized to varying lengths to accommodate different levels of immersion of the workpieces, or to accommodate different coefficients of expansion of the fluid under test, precluding the need to vent hot fluids from the testing chamber after heating. In alternative embodiments, eductor tube 871 could also be utilized as an element of a capacitive level sensing device to automatically control the level of fluid in testing chamber 801.

FIG. 2 discloses a testing chamber cap 206 which contains several conduits to facilitate passage of sensor lines and fluid into and out of testing chamber 201. FIG. 10 discloses one embodiment of a testing chamber cap that uses a minimum of through bores to provide necessary passages into and from the testing chamber. With reference to FIG. 10, cap 1006, which is the equivalent of cap 206 of FIG. 2 and its equivalents disclosed elsewhere in this document, contains two blind bored conduits 1022 and 1023, which are bored laterally through the side of cap 1006, perpendicular to the faces of cap 1006, and at roughly a bore line angle of 60 degrees apart. Conduits 1022 and 1023 meet substantially off center of cap 1006. A single blind bore conduit 1042, is through bored between the top and bottom faces of cap 1006 such that it passes through the intersection of conduits 1022 and 1023. Conduit 1042 is equivalent in function to conduit 842 of FIG. 8. Conduits 1022 and 1023, with reference to FIG. 11, are the equivalents of conduits 1179 and 1174 respectively, and their respective equivalents disclosed elsewhere in this document.

Additional features of cap 1006 is that it contains an o-ring groove on a projection extending from its bottom face to establish a seal to the walls of a testing chamber into which it is installed. This feature is illustrated with reference to FIG. 8 as o-ring 847 and o-ring groove 846 of cap 806.

With reference to FIG. 10, an additional feature of cap 1006 is a series of through bored holes 1050, 1051, 1052, 1053, 1054, and 1055. These are provided to secure the cap 1006 to a testing chamber using a flange type of fitting.

Figure 11:
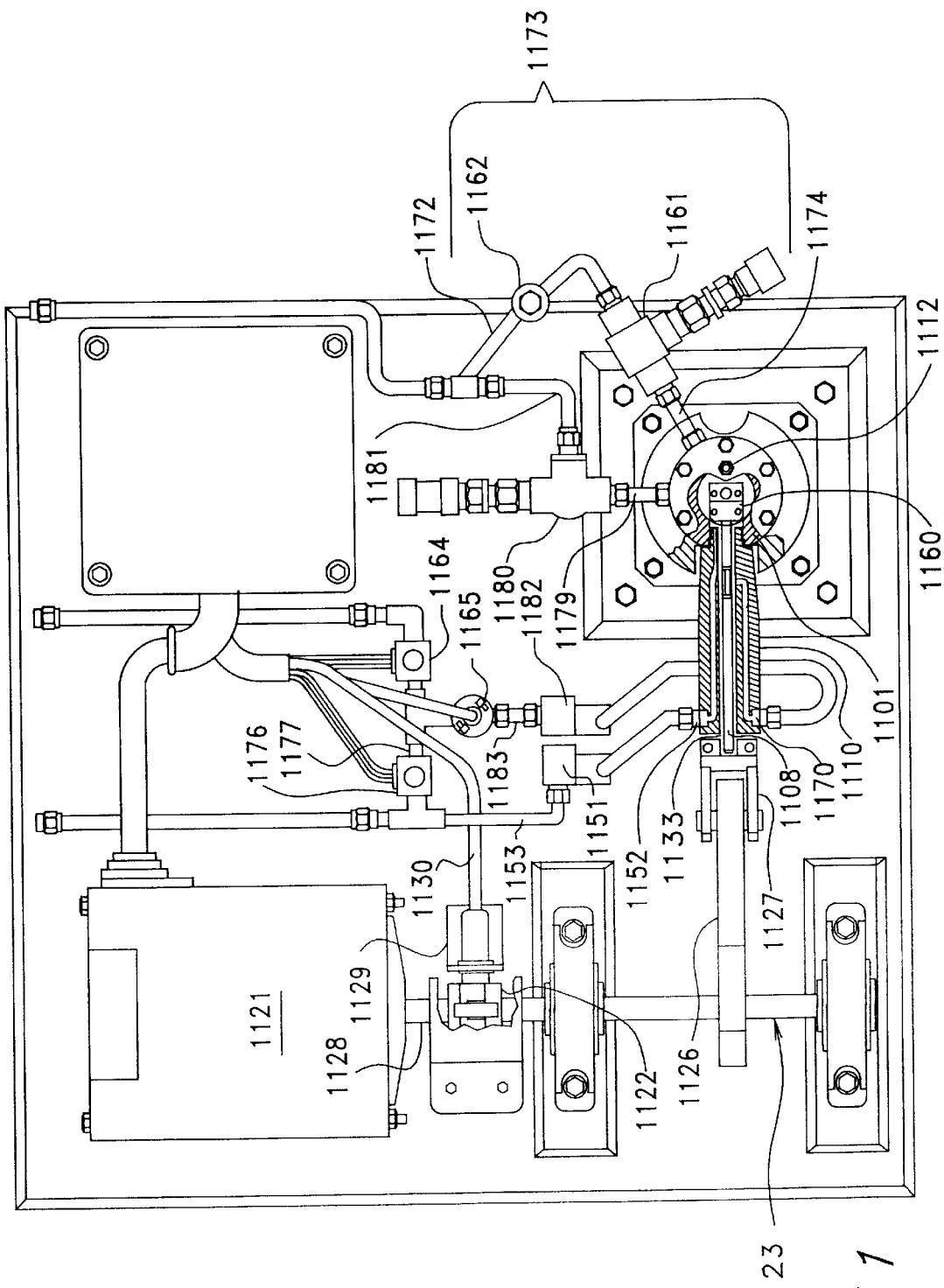
FIG. 11 is a plan view of the preferred embodiment of the testing apparatus.

FIG. 11 is a plan view of one embodiment of the present invention. With reference to FIG. 11, shown as a partial cutaway is actuator rod support arm 1110. Actuator rod support arm 1110 is equivalent to actuator rod support arm 210 of FIG. 2 and its equivalents disclosed elsewhere in this document. Actuator rod support arm 1110 has bored into it conduits 1170 and 1152. These conduits are the equivalent, with reference to FIG. 1, of conduits 170 and 152 respectively, and their respective equivalents disclosed elsewhere in this document. In like manner, valves 1151 and 1182 are the equivalent of, with reference to FIG. 1, valves 151 and 182 respectively and their respective equivalents disclosed elsewhere in this document.

With further reference to FIG. 11, valve 1176 is used to supply inert gas conduits 1177 and 1152. This feature permits purging and venting the lubricant media inlet of testing chamber 1101 with inert gas.

Testing chamber 1101 is the equivalent to testing chamber 101 of FIG. 1 and its equivalents disclosed elsewhere in this document. With further reference to FIG. 11, valve 1182 is used to supply high pressure gas to the annular space 1133 between actuator rod 1108 and the bore through actuator rod support arm 1110. Actuator rod 1108 and actuator rod support arm 1110 are equivalent to, with reference to FIG. 2, actuator rod 208 and actuator rod support arm 210 respectively, and their respective equivalents disclosed elsewhere in this document.

With reference to FIG. 11, testing chamber 1101 is sealed at it's top by cap 1106 and contains workpiece holding and contacting assembly 1160. Cap 1106 is of the design disclosed for cap 1006 of FIG. 10. Testing chamber 1101 is the equivalent of testing chamber 101 of FIG. 1 and its equivalents disclosed elsewhere in this document. Workpiece holding and contacting assembly 1160 is composed of three previously disclosed elements, a workpiece contact point loading device, a flat workpiece chuck and a spherical workpiece chuck. The workpiece contact point loading device is of the design previously disclosed for workpiece loading device 207 of FIG. 2. The flat workpiece chuck is of the design previously disclosed as flat workpiece chuck 202 of FIG. 2, and the spherical workpiece chuck is of the design previously disclosed for spherical workpiece chuck 405 of FIG. 4.

With further reference to FIG. 11, workpiece holding and contacting assembly 1160 is fastened to actuator rod 1108. Testing chamber 1101 is sealed at the point where the actuator rod 1108 passes through it by high pressure gas supplied to the annular space 1133 via conduit 1170 in the manner disclosed above for high pressure gas sealing. The actuator rod 1108 responds to motion derived from electric motor 1121 via clamping assembly 1127, crank arm 1126, and drive shaft 1123. The rotary motion of motor 1121 is converted to reciprocating motion by a rotational axis adjuster (not shown) interposed between shaft 1123 and crank arm 1126. The design of the rotational axis adjuster is that described, with reference to FIG. 9, for the nested eccentric rotational axis adjuster 933. The reciprocating motion of the rotational axis adjuster is linerized by crank arm 1126 and clamping assembly 1127. The linear motion is translated through actuator arm 1108 to the spherical workpiece chuck (not shown), the details of which are recited above. Since the flat workpiece is held stationary in the workpiece holding and contacting assembly 1160, movement of the spherical workpiece gives rise to differential motion between the flat and spherical workpieces.

Pivot connector 1127, crank arm 1126 drive shaft 1123 and motor 1121 are the equivalent, with reference to FIG. 6, of pivot connector 627, crank arm 626, drive shaft 623, and motor 621 respectively and their respective equivalents disclosed elsewhere in this document, and function in like manner as described for those elements.

With further reference to FIG. 11, flow control assembly 1173 is comprised of needle valve 1161 and stop valve 1162. Flow control assembly 1173 is equivalent to valve 173 of FIG. 1, and functions in a like manner to adjust the level of fluid contained in testing chamber 1101. In the assembly, needle valve 1161 is adjusted to control flow rate through the assembly, while stop valve 1162 is remotely actuated and controls whether or not fluid may pass through conduits 1174 and 1172 and thence to a suitable vent.

With further reference to FIG. 11, valve 1180 is a pressure relief valve of a type that is standard in the industry. The valve seat is spring loaded, the valve opening in response to a pressure condition against the seat that exceeds the spring tension brought to bear on it. It is a manual valve, the pressure at which it will open being adjusted by the apparatus operator. It acts to vent pressure from testing chamber 1101, and is the equivalent of valve 180 of FIG. 1 and its equivalents disclosed elsewhere in this document.

With further reference to FIG. 11, the rotational speed of coupling 1122 is monitored by infrared pickup 1129. Coupling 1122 is the equivalent of coupling 622 of FIG. 6 and its equivalents disclosed elsewhere in this document. Coupling 1122 is a simple cushioned plate coupling. Infrared pickup 1129 produces an electrical signal on associated control line 1130 that rises and falls as each tooth of coupling 1122 passes it. A simple counting device time averages the number of teeth per unit time that pass the pickup thereby calculating the rate of rotation of drive shaft 1123. This information is fed back to a computer which in turn adjusts the speed of motor 1121. Drive shaft 1123 and motor 1121 are equivalent, with reference to FIG. 6 to drive shaft 623 and motor 621 respectively, and their respective equivalents disclosed elsewhere in this document. An example of the motor speed control which is commercially available is a Newport P6008® controller wired to an Eaton Series A1® infrared pick-up. The operator may adjust this feed back system to give rotational speeds of 0–3600 rpm.

Not illustrated in FIG. 11 is the connection between crank arm 1126 and drive shaft 1123. In this embodiment crank arm 1126 rides upon a rotational axis adjuster of the type disclosed above, with reference to FIG. 9, as rotation axis adjuster 933. In this embodiment, with further reference to FIG. 9, hole 932 in eccentric shell 938 and hole 934 in eccentric shell 939 are both bored 0.5 millimeter off center of the eccentric shell. This provide a rotational axis adjuster capable of varying the axis of rotation between +/−0 and 1.0 millimeter off center. This rotational axis adjuster therefore is capable of imparting between 0 and 2 millimeters of linear motion to the actuator rod assembly fastened to it.

With further reference to FIG. 11, additional features of this embodiment are temperature sensor 1112 penetrating cap 1106 and sealed to it with a nut and ferrule fitting such as is well known in the industry. Temperature sensor 1112 is a thermocouple device such as is disclosed for, with reference to FIG. 7, thermocouple device 712 and its equivalents disclosed elsewhere in this document.

With further reference to FIG. 11, valve 1164, which is connected by a tee fitting to valves 1177 and 1165, permits an operator to use a common gas source to supply gas for pressurizing annular space 1133 in actuator rod support arm 1110 and to purge the lubricant media supply conduits 1152 and 1153.

Further features of this embodiment may be understood by reference to FIG. 8, a cutaway side elevation of the apparatus. Workpiece loading device 807 is of the type disclosed, with reference to FIG. 2, for workpiece loading device 207. With further reference to FIG. 8, workpiece loading device 807 is a free sliding weight located in testing chamber 701 by precise machining. With further reference to FIG. 8, workpiece loading device 807 has fastened to it flat workpiece chuck 802 which in turn clamps flat workpiece 803 in a fixed location within testing chamber 801.

With further reference to FIG. 8, this embodiment retains spherical workpiece 804, which is the equivalent of spherical workpiece 204 of FIG. 2, in spherical workpiece chuck 805. Spherical workpiece chuck 805 is fastened on actuator rod 808. Spherical workpiece chuck 805 is of the design disclosed for spherical workpiece chuck assembly 405 of FIG. 4.

Contact pressure between flat workpiece 803 and spherical workpiece 804 is generated by the weight of workpiece loading device 807. The weight of workpiece loading device 807 is permitted to bear down on the stacked workpiece chucks when workpiece loading device 807 holding flat workpiece 803 in flat workpiece chuck 802 is placed into testing chamber 801 containing spherical workpiece chuck 805 into which has been mounted spherical workpiece 804.

When the flat and spherical workpieces have been loaded into the testing chamber 801, cap 806 is secured using 6 fasteners of the type 750. A seal is made between cap 806 and testing chamber 801 via an o-ring 847 seated in groove 846 of cap 806. The details of cap 806 in this embodiment are identical to those disclosed, with reference to FIG. 10, for cap 1006.

Additional features of this embodiment which can be understood in reference to FIG. 8 are heater 895 and its associated insulating shroud 896. Heater 895 is a flat disk electrical resistance heater such as is well known in the industry. It is placed in intimate contact with the bottom of testing chamber 801 and contains an opening in the middle, giving it the appearance of a large washer. The opening in the middle permits any materials passing out of blow out panel 813 to pass through the heater and be diffused through conduit 898 out the bottom of the testing chamber 801 mounting plate 897.

Heater 895 has electric power supplied to it via cables 885. Power is supplied to heater 895 in response to signals from thermocouple 812 using a feedback control device such as is well known in the industry. Heater 895 and power leads 885 are the equivalent of, with reference to FIG. 1, heater 195 and power leads 185 respectively and their respective equivalents disclosed elsewhere in this document. The procedure used to test materials in the disclosed apparatus may best be understood with reference to FIG. 12. Step 1201 is to prepare the work faces of the workpiece materials used to test the lubricant media's lubricating properties in accordance with the testing method to be followed. In one embodiment of the testing method, ASTM testing method D6079 is followed. This test protocol calls for workpieces to be produced with specific dimensions and surface finish, and to be cleaned by a specified routine. Other types of workpieces and preparation methods are also adaptable to being tested in the disclosed apparatus of the present invention.

Figure 12:
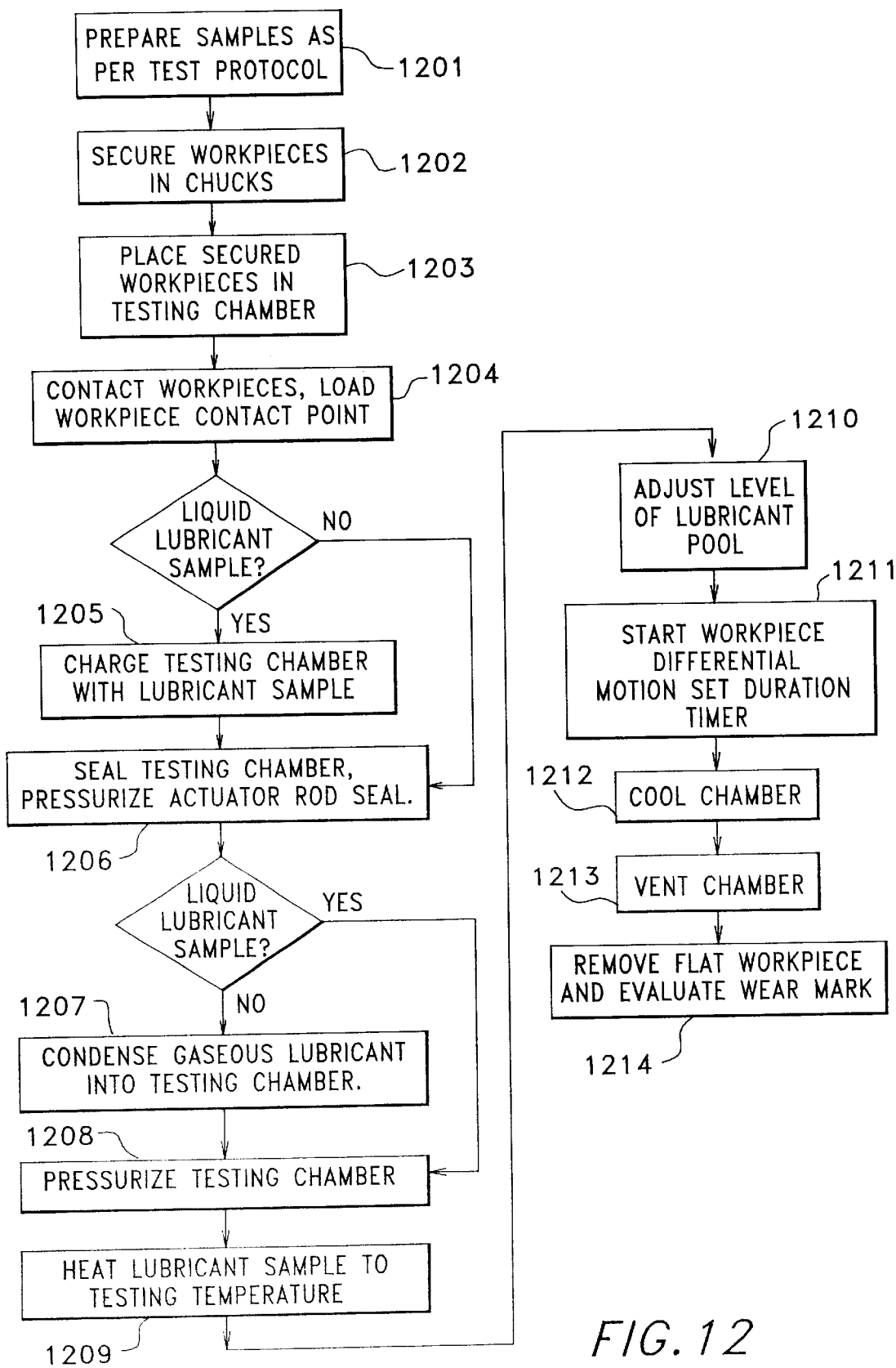
FIG. 12 is a block diagram of the testing methodology of the subject invention.

With further reference to FIG. 12, step 1202 is to fasten the workpieces used to evaluate the lubricating properties of a lubricant medium into position in the testing apparatus. In accordance with ASTM testing protocol D6079, this calls for fastening a flat workpiece into a flat workpiece chuck and a spherical workpiece into a spherical workpiece chuck. Step 1203 calls for placing the workpieces into the testing chamber. At this point any mechanical adjustments required are also made. In the best mode of practicing the present invention apparatus, the stroke length is adjusted by a double nested eccentric type of rotational axis adjuster. The stroke length is also set at this time and temperature and test duration controls are also set. In the best mode for carrying out ASTM testing protocol D6079, spherical workpiece chuck bearing the spherical workpiece is fastened to the actuator rod end residing inside the testing chamber. The flat workpiece chuck bearing the flat workpiece is fastened to the workpiece loading device and enters the chamber when the workpiece loading device is placed into the testing chamber bore. In step 1204, the workpieces are contacted and a load specified by the testing protocol being followed is applied to the contact area between the workpieces. In ASTM testing method D6079 this load is specified at 200 grams. Other testing protocols may require heavier or lighter loads. In some embodiments load is applied by a spring tension device, and in others the act of releasing the workpiece loading device once contact has been made between the workpieces loads the contact area by virtue of the weight of the combined workpiece loading device and associated workpiece chuck.

The next step depends upon whether the lubricant media being tested is a liquid or gas at standard atmospheric pressures and temperature (S.T.P.). If the lubricant media is an S.T.P. gas, step 1205 is skipped. If it is an S.T.P. liquid, step 1205 is followed and a sample of the lubricant media is placed into the testing chamber until it covers the contact area between the two workpieces.

With further reference to FIG. 12, in step 1206 the testing chamber is sealed by securing the testing chamber cap and by supplying gas pressure to the annular space between the actuator rod and the actuator rod support arm. Step 1207 is next followed only if the composition to be tested for lubricating properties is an S.T.P. gas (if step 1205 was bypassed). In this step the lubricant media is introduced into the chamber, either as a liquid under pressure, or condensed from the gas phase by cooling a portion of the testing chamber with a source of the lubricant media attached to the testing chamber. Thus if step 1207 is being followed, an amount of the lubricant is introduced into the chamber at a pressure permitting it to remain a liquid until the contact area between the workpieces is covered by the liquid introduced into the testing chamber. In step 1208, the testing chamber is pressurized with inert gas to a pressure that will simulate the conditions which the test protocol is designed to simulate when sufficient lubricant media has been charged into the testing chamber, step 1209 is carried out. The testing chamber and lubricant media is brought up to the testing temperature using the testing chamber heater and the heater controller is set to maintain the lubricant sample in the testing chamber at the temperature desired for the test. In a typical test this is less than 200 degrees C., but with the present invention apparatus may be as much as 500 degrees C.

In step 1210 the level of the lubricant media liquid contained in the testing chamber is adjusted to a level so that the contact area of the workpieces is just covered by the sample but not submerged in lubricant media. Adjustment of the liquid level is carried out using the eductor tube in the manner described above. In step 1211, following adjustment of the lubricant level, differential motion is started between the workpieces, and the motion generator is adjusted to give a stroke rate called for in the testing protocol being followed. The ASTM testing protocol D6079 calls for a cycle rate of 50.0 cycles per second. The present invention can be adjusted for rates of 0–60 cycles per second, which corresponds to drive motor revolutions of 0–3600 rpm. Once the proper cycle rate has been set, a timer is started that will shut off the driving motor at the end of the testing period. ASTM standard D6079 calls for a testing period of 75 minutes.

In step 1212, once the testing period has expired and the timer has shut off the driving motor, the chamber is cooled to room temperature. Step 1213 is then carried out in which residual pressure in the testing chamber is vented out of the testing chamber and along with it any lubricant material that is either in gas phase or has become entrained in the vent stream. After the testing chamber has been cooled to room temperature and all of the pressure has been vented from it, in step 1214 the chamber is opened and flat workpiece is removed from it. Spherical workpiece is then evaluated according, to the testing protocol being employed for wear. In ASTM testing protocol D6079 this involves measuring the major and minor axis of the elliptical scar worn into the spherical workpiece to asses how well the lubricant sample performed. Other testing protocols may employ different evaluation procedures.

Although the present invention has been described with reference to preferred embodiments, numerous modifications and variations can be made and still the result will come within the scope of the invention. No limitation with respect to the specific embodiments disclosed herein is intended or should be inferred.

We claim:

1. An apparatus for testing a wear resistance of materials and at least one lubricating property of a fluid under conditions where a workpiece is subjected to a fretting wear, said testing apparatus comprising:

a testing chamber containing a first workpiece chuck, a second workpiece chuck, and a workpiece loading device, said first workpiece chuck being in communication with said workpiece loading device such that said workpiece loading device imparts a contact force to a workpiece held within said first and second workpiece chucks, and wherein said first and second workpiece chucks are constrained to move only in a pair of axis that are perpendicular to each other;

an actuator rod passing through said testing chamber and having two ends, said first end residing in an ambient environment surrounding said testing chamber and said second end residing within said testing chamber, and wherein said second workpiece chuck is in communication with said actuator rod such that movement of said actuator rod imparts like movement to said second workpiece chuck;

a motion generator in communication with said first end of said actuator rod such that said motion generator imparts a linear cyclic motion to said actuator rod, said motion generator comprising an electric motor, a cranking assembly attached to an output shaft of said electric motor, said cranking assembly having at least one member that follows a path of eccentric rotation relative to a rotation of said output shaft, said a crank arm having two ends, a first end fastened to said cranking assembly member having a path of eccentric rotation and a second end fastened to said actuator rod first end, thereby translating the rotational motion of said electric motor output shaft into a linear reciprocal motion of said actuator rod;

a seal between said actuator rod and said testing chamber such that a fluid placed under pressure within said testing chamber will not escape from the testing chamber along the testing chamber/actuator rod interface; and at least one sealable conduit communicating with the testing chamber, whereby fluids and objects may be passed into and out from said testing chamber;

wherein said cranking assembly is comprised of two nested eccentric shells interposed between said output shaft and said crank arm first end attachment point, said inner eccentric shell having the ability to be locked to said outer eccentric shell at any point of rotation within the bore of said outer eccentric shell, thereby providing a means of adjusting the amount of eccentric rotation the outer eccentric shell exhibits relative to said output shaft which varies between twice the sum and twice the difference of the eccentric offset of the bores of said inner and said outer eccentric shells; and wherein said testing chamber is a hollow cylinder, said workpiece loading device further comprises a solid metal cylinder having an outer diameter and surface finish to permit it to slide freely within said testing chamber inner bore, and wherein contact pressure between said first and second workpieces held in said first and second workpiece chucks is generated by the weight of said workpiece loading device impinging upon a horizontal array of said workpiece chucks containing workpieces, said horizontal array of workpiece chucks being arranged such that a surface of said first workpiece resides in contact with a surface of said second workpiece.

2. The apparatus of claim 1, wherein said first workpiece chuck is fastened directly to said workpiece loading device and wherein said second workpiece chuck is fastened directly to said actuator rod.

3. The apparatus of claim 2, wherein said actuator rod to testing chamber seal is effected by appending a sealing arm to said testing chamber at the point where said actuator rod penetrates said testing chamber, and wherein said sealing arm contains a bore through which said actuator rod passes, said bore having a diameter and surface finish that provides for annular clearance between said actuator rod and said sealing arm bore when said sealing arm is interposed into said sealing arm bore that is less than 25 microns, and wherein said sealing arm has facilities for conducting high pressure fluid into the annular space between said sealing arm bore and said actuator rod residing in said sealing arm.

4. The apparatus of claim 3, wherein said sealable testing chamber conduit further comprises an opening at a top of said testing chamber, having a diameter equal to that of said testing chamber, and which is sealed with a flange and a cap seal.

5. The apparatus of claim 4, wherein said cap of said flange and said cap seal contains at least one conduit whereby a level of a fluid contained in said testing chamber may be adjusted and further contains at least one valve fastened to said conduit whereby said conduit may be sealed from an ambient environment.

6. The apparatus of claim 5, wherein the first workpiece chuck is adapted to retain a spherical workpiece meeting the requirements of ASTM testing specification D6079, the second workpiece chuck is adapted to hold a flat workpiece meeting the requirements of ASTM testing specification D 6079, the first workpiece is a spherical workpiece meeting the requirements of ASTM testing specification D6079, and the second workpiece is a flat workpiece meeting the requirements of ASTM testing specification D 6079.

7. The apparatus of claim 6, wherein the second workpiece chuck is adapted to retain a spherical workpiece meeting the requirements of ASTM testing specification D6079, the first workpiece chuck is adapted to hold a flat workpiece meeting the requirements of ASTM testing specification D 6079, the second workpiece is a spherical workpiece meeting the requirements of ASTM testing specification D6079, and the first workpiece is a flat workpiece meeting the requirements of ASTM testing specification D 6079.

8. An apparatus for testing a wear resistance of materials and at least one lubricating property of a fluid under conditions where a workpiece is subjected to a reciprocating wear, said testing apparatus comprising;

a blind bored hollow cylindrical testing chamber having a top end and a bottom end, oriented with its bore axis vertical such that the top end is the cylinder open end and the bottom end is its blind end, said hollow cylinder being fitted near its bottom end with an actuator rod support arm perpendicular to said bore axis, said actuator rod support arm having a bore of sufficient diameter to pass an end of an actuator rod there through and being fitted with a conduit suitable for passing compressed gas into said bore;

an actuator rod having two ends, a first end being passed through the bore of said actuator rod support arm and residing within said testing chamber, and a second end residing in an ambient environment surrounding said testing chamber, wherein a clearance between said first end of said actuator rod and said bore of said actuator rod support arm is less than 2 millimeters;

a first workpiece chuck adapted to hold a first workpiece which is rigidly fastened to said first end of said actuator arm;

a first workpiece rigidly fastened into said first workpiece chuck;

a workpiece loading device having a lower face and an upper face, said workpiece loading device being inserted into the bore of said testing chamber with said lower face oriented down, wherein said workpiece loading device comprises a solid metal cylinder machined to slide along the bore of said testing chamber under the influence of gravity alone, thereby descending said testing chamber bore until it contacts said first workpiece;

a second workpiece chuck adapted to hold a second workpiece, wherein said second workpiece chuck is fastened to said lower face of said sample loading device such that a workpiece fastened into said second workpiece chuck will contact a first workpiece fastened into said first workpiece chuck when said sample loading device is passed down the bore of said testing chamber;

a second workpiece fastened into said second workpiece chuck;

a pivot clamp fastened to said second end of said actuator rod;

a crank arm having two ends, a driving end and a driven end, wherein said driven end is fastened to said pivot clamp;

a cranking assembly fastened to said driving end of said crank arm;

a drive shaft fastened to said cranking assembly such that rotation of the drive shaft is translated to reciprocating motion of said crank arm by said cranking assembly;

an electric motor fastened to said drive shaft; and a cap providing a compression seal fastened to said top end of said testing chamber, said compression seal being able to withstand in excess of 200 psi of pressure without leaking.

9. The apparatus of claim 8, wherein said bottom end of said testing chamber is fitted with a blow out panel.

10. The apparatus of claim 8, wherein the first workpiece chuck is adapted to retain a spherical workpiece meeting the requirements of ASTM testing specification D6079, the second workpiece chuck is adapted to hold a flat workpiece meeting the requirements of ASTM testing specification D 6079, the first workpiece is a spherical workpiece meeting the requirements of ASTM testing specification D6079, and the second workpiece is a flat workpiece meeting the requirements of ASTM testing specification D 6079.

11. The apparatus of claim 8, wherein the second workpiece chuck is adapted to retain a spherical workpiece meeting the requirements of ASTM testing specification D6079, the first workpiece chuck is-adapted to hold a flat workpiece meeting the requirements of ASTM testing specification D 6079, the second workpiece is a spherical workpiece meeting the requirements of ASTM testing specification D6079, and the first workpiece is a flat workpiece meeting the requirements of ASTM testing specification D 6079.

12. The apparatus of claim 8, wherein said cranking assembly comprises two nested eccentric shells interposed between said drive shaft and said crank arm driven end, said inner eccentric shell having the ability to be locked to said outer eccentric shell at any point of rotation within the bore of said outer eccentric shell, thereby providing a means of adjusting the amount of eccentric rotation the outer eccentric shell exhibits relative to said drive shaft which varies between twice the sum and twice the difference of the eccentric offset of the bores of said inner and said outer eccentric shells.

13. A method of testing at least one lubrication property of a fluid that is a liquid at S.T.P. conditions using a sealed testing chamber adapted to simulate an environment encountered in an operating engine, said method comprising the steps of:

preparing a workface of a first workpiece;

fastening said first workpiece into a first chuck;

placing said first chuck containing said first workpiece into a testing chamber;

fastening said first chuck containing said first workpiece to an end of an actuator rod contained within said testing chamber, said actuator rod being capable of imparting a linear movement to said first chuck and thereby moving said first workpiece;

preparing a workface of a second workpiece;

fastening said second workpiece into a second chuck;

fastening said second chuck containing said second workpiece to a workpiece loading device;

contacting said first workpiece workface with said second workpiece workface;

imparting a load to a point of contact between said first and second workpieces with a workpiece loading device;

immersing said workpiece contact point in a lubricating media;

sealing said testing chamber;

pressurizing said testing chamber to a selected pressure;

heating said lubricating media to a selected temperature;

imparting a differential linear motion to said workpieces at said workpiece contact point until a measurable scar is imparted to at least one workpiece workface;

venting said pressure from said testing chamber;

removing said workpiece having a measurable scar on said workface from said testing chamber; and evaluating said workface scar;

wherein said workpiece loading device is a weighted cylinder to which said second chuck is fastened, and wherein a load is applied to said contact area between said first workpiece and said second workpiece contact point by gravity acting on said workpiece loading device which is permitted to slide freely in said testing chamber after contact is established between said first and second workpiece workfaces.

14. The testing method of claim 13, wherein said motion generator is a motor operating a crank arm through a double eccentric rotation axis adjuster.

15. A method of testing the lubricating properties of a fluid lubricating media which is not a liquid at S.T.P. conditions using a sealed testing chamber adapted to simulate an environment encountered in an operating engine, said method comprising the steps of:

preparing a workface of a first workpiece;

fastening said first workpiece into a first chuck;

placing said first chuck containing said first workpiece into a testing chamber;

fastening said first chuck containing said first workpiece to an end of an actuator rod contained within said testing chamber, said actuator rod being capable of imparting a linear movement to said first chuck and thereby moving first workpiece;

preparing a workface of a second workpiece;

fastening said second workpiece into a second chuck;

fastening said second chuck containing said second workpiece to a workpiece loading device;

contacting said first workpiece workface with said second workpiece workface;

imparting a load to a point of contact between said first and second workpieces with a workpiece loading device;

sealing said testing chamber;

charging the test chamber with an S.T.P. gas lubricant media condensate of sufficient volume to immerse said contact point between said workfaces;

pressurizing said testing chamber to a selected pressure;

heating said lubricating media to a selected temperature;

imparting a differential linear motion to said workpieces at said workpiece contact point until a measurable scar is imparted to at least one workpiece workface;

venting said pressure from said testing chamber;

removing said workpiece having a measurable scar on said workface from said testing chamber; and evaluating said workface scar;

wherein said workpiece loading device is a weighted cylinder to which said second chuck is fastened, and wherein load is applied to said contact area between said flat workpiece and said spherical workpiece by gravity acting on said workpiece loading device which is permitted to slide freely in said testing chamber after contact is established between said flat workpiece and said spherical workpiece.

16. The testing method of claim 15, wherein said motion is imparted using a motion generator, said motion generator being comprised of a motor operating a crank arm through a double eccentric rotation axis adjuster.

17. A wear testing apparatus comprising:

a test chamber having a workpiece holder holding a first workpiece in contact with a second workpiece;

a workpiece loading device applying a controlled force to a contact point between the first and second workpiece; and a motion generator connected to said workpiece holder, said motion generator imparting cyclic differential motion to said first and second workpieces, said motion describing a line at the contact point between the first and second workpiece, thereby forming a measurable scar in at least one workpiece;

said motion generator comprising an actuator rod support arm comprising an inner end in mechanical communication with said workpiece holder and extending outside of said test chamber to an opposed end, said actuator rod support arm comprising a longitudinal bore therethrough retaining an actuator rod, said longitudinal bore and said opposed end being in fluid communication with a conduit adapted to provide a pressurized gas to said longitudinal bore, said actuator rod being at deviation from linearity through said longitudinal bore and at a clearance through said longitudinal retaining bore wherein a combination of said clearance, said deviation from linearity and said pressurized gas is effective to maintain a seal effective to prevent a fluid placed under pressure within said testing chamber to escape from said testing chamber along an interface between said testing chamber and said actuator rod while permitting said actuator rod to move freely through said actuator rod support arm;

a sealable conduit affixed to said testing chamber, whereby fluids may be conducted to and from the interior of said testing chamber; and a heater affixed to said testing chamber, wherein energizing said heater raises a temperature of said workpieces and the fluids;

wherein said clearance is 50 microns or less and said deviation from linearity is less than 100 microns.

18. The testing apparatus of claim 17 wherein said motion generator further comprises an electric motor having an output shaft coupled to a rotation axis adjuster, said rotation axis adjuster being further fastened to said actuator rod using a crank arm, said rotation axis adjuster translating rotary motion of said electric motor output shaft to reciprocating motion, said crank arm translating said reciprocating motion to linear cyclic motion.

19. The testing apparatus of claim 18 wherein said rotation axis adjuster further comprises a locking, nested set of eccentrics interposed between said output shaft and said crank arm, and wherein the amplitude of reciprocation imparted by the rotation axis adjuster is variable by rotating said nested eccentrics relative to each other.

20. A wear testing apparatus comprising:
a test chamber having a workpiece holder holding a first workpiece in contact with a second workpiece;
a workpiece loading device applying a controlled force to a contact point between the first and second workpiece; and
a motion generator connected to said workpiece holder, said motion generator imparting cyclic differential motion to said first and second workpieces, said motion describing a line at the contact point between the first and second workpiece, thereby forming a measurable scar in at least one workpiece;
said motion generator comprising an actuator rod support arm comprising an inner end in mechanical communication with said workpiece holder and extending outside of said test chamber to an opposed end, said actuator rod support arm comprising a longitudinal bore therethrough retaining an actuator rod, said actuator rod comprising one or more feature selected from the group consisting of a deviation from linearity through said longitudinal retaining bore and a clearance through said longitudinal retaining bore, said one or more feature being effective to maintain a seal effective to prevent a fluid placed under pressure within said testing chamber to escape from said testing chamber along an interface between said testing chamber and said actuator rod while permitting said actuator rod to move freely through said actuator rod support arm;
further comprising at least one sealable conduit communicating with the testing chamber, whereby fluids and objects may be passed into and out from said testing chamber.

21. The apparatus of claim 20 wherein said clearance is 50 microns or less and said deviation from linearity is less than 100 microns.

22. The testing apparatus of claim 21 wherein said motion generator further comprises an electric motor having an output shaft coupled to a rotation axis adjuster, said rotation axis adjuster being further fastened to said actuator rod using a crank arm, said rotation axis adjuster translating rotary motion of said electric motor output shaft to reciprocating motion, said crank arm translating said reciprocating motion to linear cyclic motion.

23. The testing apparatus of claim 22 wherein said rotation axis adjuster further comprises a locking, nested set of eccentrics interposed between said output shaft and said crank arm, and wherein the amplitude of reciprocation imparted by the rotation axis adjuster is variable by rotating said nested eccentrics relative to each other.

24. The apparatus of claim 20 wherein said motion generator further comprises an electric motor, a cranking assembly attached to an output shaft of said electric motor, said cranking assembly having at least one member that follows a path of eccentric rotation relative to a rotation of said output shaft, and a crank arm having two ends, a first end fastened to said cranking assembly member having a path of eccentric rotation and a second end fastened to said actuator rod first end, thereby translating the rotational motion of said electric motor output shaft into a linear reciprocal motion of said actuator rod.

25. The testing apparatus of claim 24 wherein said rotation axis adjuster further comprises a locking, nested set of eccentrics interposed between said output shaft and said crank arm, and wherein the amplitude of reciprocation imparted by the rotation axis adjuster is variable by rotating said nested eccentrics relative to each other.

26. The apparatus of claim 20 wherein said sealable testing chamber conduit further comprises an opening at a top of said testing chamber, having a diameter equal to that of said testing chamber, and which is sealed with a flange and a cap seal.

27. The apparatus of claim 26 further comprising at least one sealable conduit communicating with the testing chamber, whereby fluids and objects may be passed into and out from said testing chamber.

28. The testing apparatus of claim 26 wherein said clearance is 50 microns or less and said deviation from linearity is less than 100 microns.

29. The testing apparatus of claim 26 wherein said cap of said flange and said cap seal contains at least one conduit whereby a level of a fluid contained in said testing chamber may be adjusted and further contains at least one valve fastened to said conduit where by said conduit may be sealed from an ambient environment.

30. The apparatus of claim 20 wherein said sealable testing chamber conduit further comprises an opening at a top of said testing chamber, having a diameter equal to that of said testing chamber, and which is sealed with a flange and a cap seal.

31. The apparatus of claim 30 wherein said cap of said flange and said cap seal contains at least one conduit whereby a level of a fluid contained in said testing chamber may be adjusted and further contains at least one valve fastened to said conduit where by said conduit may be sealed from an ambient environment.

32. The apparatus of claim 20 wherein the first workpiece holder is adapted to retain a spherical workpiece meeting the requirements of ASTM testing specification D 6079, the first workpiece is a spherical workpiece meeting the requirements of ASTM testing specification D 6079, and the second workpiece is a flat workpiece the requirements of ASTM testing specification D 6079.

33. A wear testing apparatus comprising:
a test chamber having a workpiece holder holding a first workpiece in contact with a second workpiece;
a workpiece loading device applying a controlled force to a contact point between the first and second workpiece; and
a motion generator connected to said workpiece holder, said motion generator imparting cyclic differential motion to said first and second workpieces, said motion describing a line at the contact point between the first and second workpiece, thereby forming a measurable scar in at least one workpiece;

said motion generator comprising an actuator rod support arm comprising an inner end in mechanical communication with said workpiece holder and extending outside of said test chamber to an opposed end, said actuator rod support arm comprising a longitudinal bore therethrough retaining an actuator rod, said longitudinal bore and said opposed end being in fluid communication with a conduit adapted to provide a pressurized gas to said longitudinal bore, said actuator rod comprising one or more feature selected from the group consisting of a deviation from linearity through said longitudinal bore and a clearance through said longitudinal retaining bore wherein a combination of said one or more features and said pressurized gas is effective to maintain a seal effective to prevent a fluid placed under pressure within said testing chamber to escape from said testing chamber along an interface between said testing chamber and said actuator rod while permitting said actuator rod to move freely through said actuator rod support arm;

further comprising at least one sealable conduit communicating with the testing chamber, whereby fluids and objects may be passed into and out from said testing chamber.

34. The apparatus of claim 33 wherein said clearance is 50 microns or less and said deviation from linearity is less than 100 microns.

35. The testing apparatus of claim 34 wherein said motion generator further comprises an electric motor having an output shaft coupled to a rotation axis adjuster, said rotation axis adjuster being further fastened to said actuator rod using a crank arm, said rotation axis adjuster translating rotary motion of said electric motor output shaft to reciprocating motion, said crank arm translating said reciprocating motion to linear cyclic motion.

36. The testing apparatus of claim 33 wherein said motion generator further comprises an electric motor having an output shaft coupled to a rotation axis adjuster, said rotation axis adjuster being further fastened to said actuator rod using a crank arm, said rotation axis adjuster translating rotary motion of said electric motor output shaft to reciprocating motion, said crank arm translating said reciprocating motion to linear cyclic motion.

37. The testing apparatus of claim 36 wherein said rotation axis adjuster further comprises a locking, nested set of eccentrics interposed between said output shaft and said crank arm, and wherein the amplitude of reciprocation imparted by the rotation axis adjuster is variable by rotating said nested eccentrics relative to each other.

38. The testing apparatus of claim 36 wherein said rotation axis adjuster further comprises a locking, nested set of eccentrics interposed between said output shaft and said crank arm, and wherein the amplitude of reciprocation imparted by the rotation axis adjuster is variable by rotating said nested eccentrics relative to each other.

39. The apparatus of claim 33 wherein said motion generator further comprises an electric motor, a cranking assembly attached to an output shaft of said electric motor, said cranking assembly having at least one member that follows a path of eccentric rotation relative to a rotation of said output shaft, and a crank arm having two ends, a first end fastened to said cranking assembly member having a path of eccentric rotation and a second end fastened to said actuator rod first end, thereby translating the rotational motion of said electric motor output shaft into a linear reciprocal motion of said actuator rod.

40. The apparatus of claim 39 wherein said cranking assembly is comprised of two nested eccentric shells interposed between said output shaft and said crank arm first end attachment point, said inner eccentric shell having the ability to be locked to said outer eccentric shell at any point of rotation within the bore of said outer eccentric shell, thereby providing a means of adjusting the amount of eccentric rotation the outer eccentric shell exhibits relative to said output shaft which varies between twice the sum and twice the difference of the eccentric offset of the bores of said inner and said outer eccentric shells.

41. The apparatus of claim 33 wherein said sealable testing chamber conduit further comprises an opening at a top of said testing chamber, having a diameter equal to that of said testing chamber, and which is sealed with a flange and a cap seal.

42. The apparatus of claim 41 wherein said cap of said flange and said cap seal contains at least one conduit whereby a level of a fluid contained in said testing chamber may be adjusted and further contains at least one valve fastened to said conduit where by said conduit may be sealed from an ambient environment.

43. A wear testing apparatus comprising:

a test chamber having a workpiece holder holding a first workpiece in contact with a second workpiece;

a workpiece loading device applying a controlled force to a contact point between the first and second workpiece; and a motion generator connected to said workpiece holder, said motion generator imparting cyclic differential motion to said first and second workpieces, said motion describing a line at the contact point between the first and second workpiece, thereby forming a measurable scar in at least one workpiece;

said motion generator comprising an actuator rod support arm comprising an inner end in mechanical communication with said workpiece holder and extending outside of said test chamber to an opposed end, said actuator rod support arm comprising a longitudinal bore therethrough retaining an actuator rod, said actuator rod comprising one or more feature selected from the group consisting of a deviation from linearity through said longitudinal retaining bore and a clearance through said longitudinal retaining bore, said one or more feature being effective to maintain a seal effective to prevent a fluid placed under pressure within said testing chamber to escape from said testing chamber along an interface between said testing chamber and said actuator rod while permitting said actuator rod to move freely through said actuator rod support arm;

wherein said testing chamber is a hollow cylinder, said workpiece loading device further comprises a solid metal cylinder having an outer diameter and surface finish to permit it to slide freely within said testing chamber inner bore, and wherein contact pressure between said first and second workpieces held in said first and second workpiece holders is generated by the weight of said work piece loading device impinging upon a horizontal array of said workpiece holders containing workpieces, said horizontal array of workpiece holders being arranged such that a surface of said first workpiece resides in contact with a surface of said second workpiece.

44. The apparatus of claim 43 wherein said clearance is 50 microns or less and said deviation from linearity is less than 100 microns.

45. The testing apparatus of claim 44 wherein said motion generator further comprises an electric motor having an output shaft coupled to a rotation axis adjuster, said rotation axis adjuster being further fastened to said actuator rod using a crank arm, said rotation axis adjuster translating rotary motion of said electric motor output shaft to reciprocating motion, said crank arm translating said reciprocating motion to linear cyclic motion.

46. The testing apparatus of claim 45 wherein said rotation axis adjuster further comprises a locking, nested set of eccentrics interposed between said output shaft and said crank arm, and wherein the amplitude of reciprocation imparted by the rotation axis adjuster is variable by rotating said nested eccentrics relative to each other.

47. The testing apparatus of claim 43 wherein said motion generator further comprises an electric motor having an output shaft coupled to a rotation axis adjuster, said rotation axis adjuster being further fastened to said actuator rod using a crank arm, said rotation axis adjuster translating rotary motion of said electric motor output shaft to reciprocating motion, said crank arm translating said reciprocating motion to linear cyclic motion.

48. The testing apparatus of claim 47 wherein said rotation axis adjuster further comprises a locking, nested set of eccentrics interposed between said output shaft and said crank arm, and wherein the amplitude of reciprocation imparted by the rotation axis adjuster is variable by rotating said nested eccentrics relative to each other.

49. The testing apparatus of claim 43 wherein said motion generator further comprises an electric motor having an output shaft coupled to a rotation axis adjuster, said rotation axis adjuster being further fastened to said actuator rod using a crank arm, said rotation axis adjuster translating rotary motion of said electric motor output shaft to reciprocating motion, said crank arm translating said reciprocating motion to linear cyclic motion.

50. The apparatus of claim 43 further comprising at least one sealable conduit communicating with the testing chamber, whereby fluids and objects may be passed into and out from said testing chamber.

51. The apparatus of claim 43 wherein said sealable testing chamber conduit further comprises an opening at a top of said testing chamber, having a diameter equal to that of said testing chamber, and which is sealed with a flange and a cap seal.

52. The apparatus of claim 51 wherein said cap of said flange and said cap seal contains at least one conduit whereby a level of a fluid contained in said testing chamber may be adjusted and further contains at least one valve fastened to said conduit where by said conduit may be sealed from an ambient environment.

53. The apparatus of claim 43 wherein the first workpiece holder is adapted to retain a spherical workpiece meeting the requirements of ASTM testing specification D 6079, the first workpiece is a spherical workpiece meeting the requirements of ASTM testing specification D 6079, and the second workpiece is a flat workpiece the requirements of ASTM testing specification D 6079.

54. A wear testing apparatus comprising:
a test chamber having a workpiece holder holding a first workpiece in contact with a second workpiece;
a workpiece loading device applying a controlled force to a contact point between the first and second workpiece; and
a motion generator connected to said workpiece holder, said motion generator imparting cyclic differential motion to said first and second workpieces, said motion describing a line at the contact point between the first and second workpiece, thereby forming a measurable scar in at least one workpiece;
said motion generator comprising an actuator rod support arm comprising an inner end in mechanical communication with said workpiece holder and extending outside of said test chamber to an opposed end, said actuator rod support arm comprising a longitudinal bore therethrough retaining an actuator rod, said longitudinal bore and said opposed end being in fluid communication with a conduit adapted to provide a pressurized gas to said longitudinal bore, said actuator rod comprising one or more feature selected from the group consisting of a deviation from linearity through said longitudinal bore and a clearance through said longitudinal retaining bore wherein a combination of said one or more features and said pressurized gas is effective to maintain a seal effective to prevent a fluid placed under pressure within said testing chamber to escape from said testing chamber along an interface between said testing chamber and said actuator rod while permitting said actuator rod to move freely through said actuator rod support arm;
wherein said testing chamber is a hollow cylinder, said workpiece loading device further comprises a solid metal cylinder having an outer diameter and surface finish to permit it to slide freely within said testing chamber inner bore, and wherein contact pressure between said first and second workpieces held in said first and second workpiece holders is generated by the weight of said work piece loading device impinging upon a horizontal array of said workpiece holders containing workpieces, said horizontal array of workpiece holders being arranged such that a surface of said first workpiece resides in contact with a surface of said second workpiece.

55. The testing apparatus of claim 54 wherein said clearance is 50 microns or less and said deviation from linearity is less than 100 microns.

56. The testing apparatus of claim 54 wherein said motion generator further comprises an electric motor having an output shaft coupled to a rotation axis adjuster, said rotation axis adjuster being further fastened to said actuator rod using a crank arm, said rotation axis adjuster translating rotary motion of said electric motor output shaft to reciprocating motion, said crank arm translating said reciprocating motion to linear cyclic motion.

57. The testing apparatus of claim 56 wherein said rotation axis adjuster further comprises a locking, nested set of eccentrics interposed between said output shaft and said crank arm, and wherein the amplitude of reciprocation imparted by the rotation axis adjuster is variable by rotating said nested eccentrics relative to each other.

58. The apparatus of claim 54 further comprising at least one sealable conduit communicating with the testing chamber, whereby fluids and objects may be passed into and out from said testing chamber.

59. The apparatus of claim 54 wherein said first workpiece holder is fastened directly to said workpiece loading device and wherein said second workpiece holder is fastened directly to said actuator rod.

60. The apparatus of claim 54 wherein the first workpiece holder is adapted to retain a spherical workpiece meeting the requirements of ASTM testing specification D 6079, the first workpiece is a spherical workpiece meeting the requirements of ASTM testing specification D 6079, and the second workpiece is a flat workpiece the requirements of ASTM testing specification D 6079.

* * * * *

UNITED STATES PATENT AND TRADEMARK OFFICE
CERTIFICATE OF CORRECTION

PATENT NO.    : 6,546,782 B1
DATED         : April 15, 2003
INVENTOR(S)   : Jose De La Cruz and Paul Lacey It is certified that error appears in the above-identified patent and that said Letters Patent is hereby corrected as shown below:

<u>Title page,</u>
Item [75], Inventor, please add the following: -- James Ohi, Denver, CO (US) --

Signed and Sealed this

Seventeenth Day of February, 2004

JON W. DUDAS
*Acting Director of the United States Patent and Trademark Office*